(12) United States Patent
Blennow et al.

(10) Patent No.: US 12,117,456 B2
(45) Date of Patent: Oct. 15, 2024

(54) METHODS FOR DETECTING AN INDIVIDUAL AS BEING AT RISK OF DEVELOPING A NEURODEGENERATIVE DISEASE

(71) Applicant: Brain Biomarker Solutions in Gothenburg AB, Gothenburg (SE)

(72) Inventors: Kaj Blennow, Kungsbacka (SE); Henrik Zetterberg, Mölnlycke (SE)

(73) Assignee: Brain Biomarker Solutions in Gothenburg AB, Gothenburg (SE)

( * ) Notice: Subject to any disclaimer, the term of this patent is extended or adjusted under 35 U.S.C. 154(b) by 0 days.

(21) Appl. No.: 16/348,037

(22) PCT Filed: Nov. 9, 2017

(86) PCT No.: PCT/EP2017/078759
§ 371 (c)(1),
(2) Date: May 7, 2019

(87) PCT Pub. No.: WO2018/087229
PCT Pub. Date: May 17, 2018

(65) Prior Publication Data
US 2019/0277864 A1  Sep. 12, 2019

(30) Foreign Application Priority Data
Nov. 10, 2016  (EP) ..................................... 16002379

(51) Int. Cl.
*G01N 33/68* (2006.01)
(52) U.S. Cl.
CPC . *G01N 33/6896* (2013.01); *G01N 2800/2821* (2013.01); *G01N 2800/50* (2013.01)
(58) Field of Classification Search
CPC ........... G01N 33/6896; G01N 2800/50; G01N 2800/2821
See application file for complete search history.

(56) References Cited

U.S. PATENT DOCUMENTS

| 5,283,173 | A | 2/1994 | Fields et al. |
| 5,468,614 | A | 11/1995 | Fields et al. |
| 5,543,112 | A | 8/1996 | Ghead et al. |
| 5,935,779 | A | 8/1999 | Massey et al. |
| 6,316,607 | B1 | 11/2001 | Massey et al. |
| 2014/0228240 | A1 | 8/2014 | Hu |
| 2015/0119278 | A1 | 4/2015 | Goetzl |

FOREIGN PATENT DOCUMENTS

EP         2950102 A1   12/2015

OTHER PUBLICATIONS

Gaiottino et al., "Increased Neurofilament Light Chain Blood Levels in Neurodegenerative Neurological Diseases," PLOS One. 8(9): e75091 (2013).
Meeter et al., "Neurofilament light chain: a biomarker for genetic frontotemporal dementia," Annals of Clinical and Translational Neurology. 3(8): 623-636 (2016).
Bacioglu et al., "Neurofilament Light Chain in Blood and CSF as Marker of Disease Progression in Mouse Models and in Neurodegenerative Diseases," Neuron. 91(1): 56-66 (2016).
International Preliminary Report on Patentability for International Application No. PCT/EP2017/078759, mailed May 14, 2019 (7 pages).
Bateman RJ, Aisen PS, De Strooper B, et al. Autosomal-dominant Alzheimer's disease: a review and proposal for the prevention of Alzheimer's disease. Alzheimers Res Ther. 2011;3(1):1.
Bateman RJ, Xiong C, Benzinger TL, et al. Clinical and biomarker changes in dominantly inherited Alzheimer's disease. N Engl J Med 2012;367:795-804 (2012).
Consensus report of the Working Group on: "Molecular and Biochemical Markers of Alzheimer's Disease". The Ronald and Nancy Reagan Research Institute of the Alzheimer's Association and the National Institute on Aging Working Group [published correction appears in Neurobiol Aging May-Jun. 1998;19(3):285]. Neurobiol Aging. 1998;19(2):109-116 (1998).
Fernandez-Martos CM, King AE, Atkinson RA, Woodhouse A, Vickers JC. Neurofilament light gene deletion exacerbates amyloid, dystrophic neurite, and synaptic pathology in the APP/PS1 transgenic model of Alzheimer's disease. Neurobiol Aging. 2015;36(10):2757-2767 (2015).
Florkowski CM. Sensitivity, specificity, receiver-operating characteristic (ROC) curves and likelihood ratios: communicating the performance of diagnostic tests. Clin Biochem Rev. 2008;29 Suppl 1(Suppl 1):S83-S87.
Fox NC, Warrington EK, Seiffer AL, Agnew SK, Rossor MN. Presymptomatic cognitive deficits in individuals at risk of familial Alzheimer's disease. A longitudinal prospective study. Brain. 1998;121( Pt 9):1631-1639 (1998).
Freeborough PA, Fox NC, Kitney RI. Interactive algorithms for the segmentation and quantitation of 3-D MRI brain scans. Comput Methods Programs Biomed. 1997;53(1):15-25 (1997).
Freeborough PA, Fox NC. The boundary shift integral: an accurate and robust measure of cerebral volume changes from registered repeat MRI. IEEE Trans Med Imaging. 1997;16(5):623-629 (1997).
Gisslén M, Price RW, Andreasson U, et al. Plasma Concentration of the Neurofilament Light Protein (NFL) is a Biomarker of CNS Injury in HIV Infection: A Cross-Sectional Study [published correction appears in EBioMedicine. May 2016;7:287-288]. EBioMedicine. 2015;3:135-140 (2015).
Hall S, Öhrfelt A, Constantinescu R, et al. Accuracy of a panel of 5 cerebrospinal fluid biomarkers in the differential diagnosis of patients with dementia and/or parkinsonian disorders. Arch Neurol. 2012;69(11):1445-1452 (2012).

(Continued)

*Primary Examiner* — Olga N Chernyshev
(74) *Attorney, Agent, or Firm* — Clark & Elbing LLP

(57) ABSTRACT

The present invention relates to a method for detecting an individual as being at risk of developing a neurodegenerative disease, the method comprising: a) measuring the amount or concentration of neurofilament-light (NfL) in a sample obtained from the individual; and b) detecting the individual as being at risk of developing the disease by comparing the amount or concentration determined in step (a) to the amount or concentration of NfL in a control, wherein an increased value of NfL relative to the control is indicative of the future development of the disease, as well as to uses related thereto.

14 Claims, 6 Drawing Sheets

(56) References Cited

OTHER PUBLICATIONS

Figure 1:
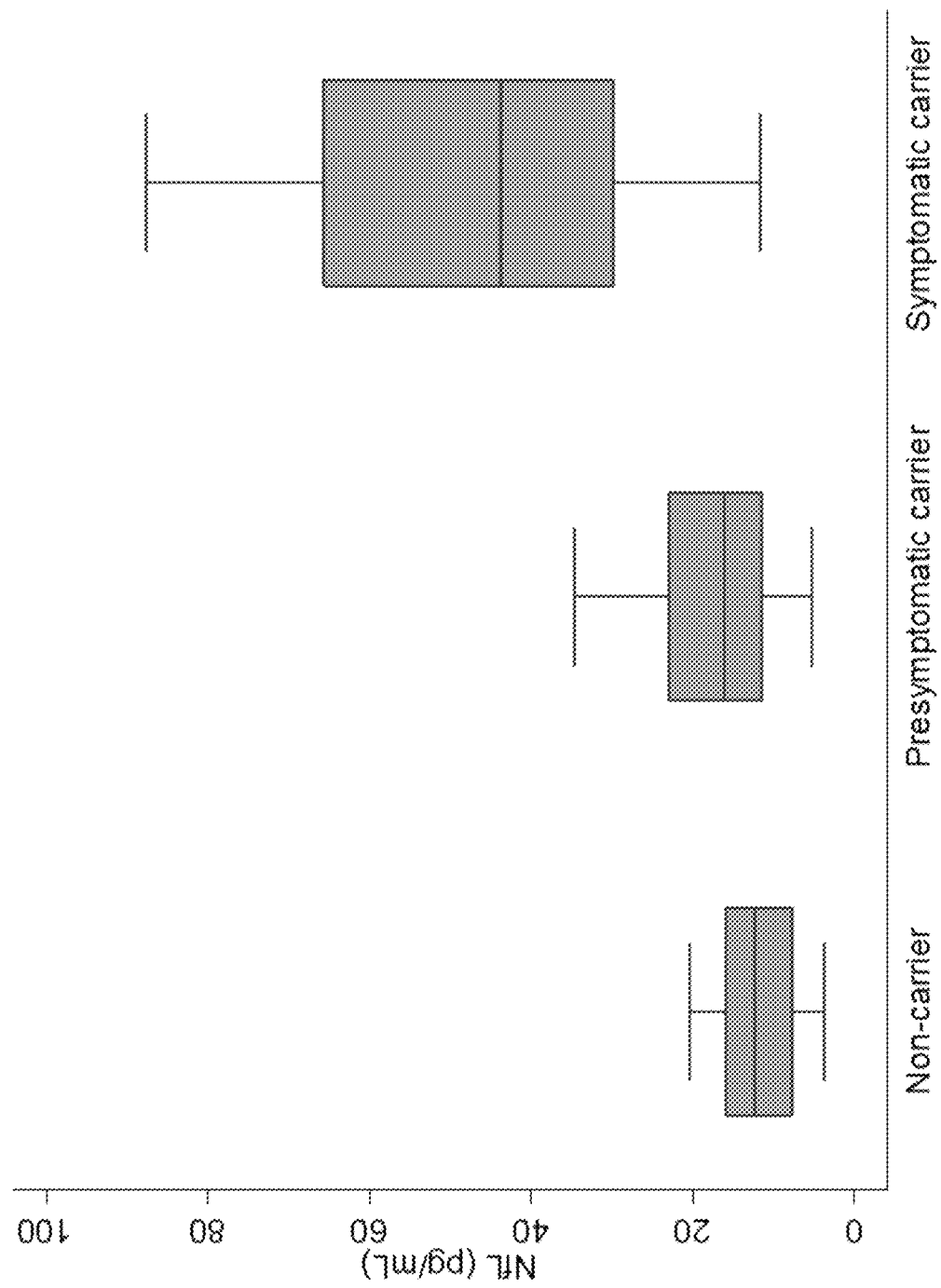

International Preliminary Report on Patentability for International Application No. PCT/EP2017/078759, issued May 14, 2019 (7 pages).

International Search Report and Written Opinion for International Application No. PCT/EP2017/078759, mailed Dec. 4, 2017 (10 pages).

Jack CR Jr, Knopman DS, Jagust WJ, et al. Hypothetical model of dynamic biomarkers of the Alzheimer's pathological cascade. Lancet Neurol. 2010;9(1):119-128 (2010).

Kuhle J, Barro C, Andreasson U, et al. Comparison of three analytical platforms for quantification of the neurofilament light chain in blood samples: ELISA, electrochemiluminescence immunoassay and Simoa. Clin Chem Lab Med. 2016;54(10):1655-1661 (2016).

Lee MK, Xu Z, Wong PC, Cleveland DW. Neurofilaments are obligate heteropolymers in vivo. J Cell Biol. 1993;122(6):1337-1350 (1993).

Lista S, O'Bryant SE, Blennow K, et al. Biomarkers in Sporadic and Familial Alzheimer's Disease. J Alzheimers Dis. 2015;47(2):291-317 (2015).

Meeter et al., "Neurofilament light chain: a biomarker for genetic frontotemporal dementia," Ann Clin Transl Neurol. 3(8): 623-636 (2016).

Olsson B, Lautner R, Andreasson U, et al. CSF and blood biomarkers for the diagnosis of Alzheimer's disease: a systematic review and meta-analysis. Lancet Neurol. 2016;15(7):673-684 (2016).

Rissin DM, Kan CW, Campbell TG, et al. Single-molecule enzyme-linked immunosorbent assay detects serum proteins at subfemtomolar concentrations. Nat Biotechnol. 2010;28(6):595-599 (2010).

Rohrer JD, Woollacott IO, Dick KM, et al. Serum neurofilament light chain protein is a measure of disease intensity in frontotemporal dementia. Neurology. 2016;87(13):1329-1336 (2016).

Rojas JC, Karydas A, Bang J, et al. Plasma neurofilament light chain predicts progression in progressive supranuclear palsy. Ann Clin Transl Neurol. 2016;3(3):216-225 (2016).

Ryman DC, Acosta-Baena N, Aisen PS, et al. Symptom onset in autosomal dominant Alzheimer disease: a systematic review and meta-analysis. Neurology. 2014;83(3):253-260 (2014).

Scherling CS, Hall T, Berisha F, et al. Cerebrospinal fluid neurofilament concentration reflects disease severity in frontotemporal degeneration. Ann Neurol. 2014;75(1):116-126 (2014).

Sjögren M, Blomberg M, Jonsson M, et al. Neurofilament protein in cerebrospinal fluid: a marker of white matter changes. J Neurosci Res. 2001;66(3):510-516 (2001).

Sperling RA, Aisen PS, Beckett LA, et al. Toward defining the preclinical stages of Alzheimer's disease: recommendations from the National Institute on Aging-Alzheimer's Association workgroups on diagnostic guidelines for Alzheimer's disease. Alzheimers Dement. 2011;7(3):280-292 (2011).

Sperling RA, Jack CR Jr, Aisen PS. Testing the right target and right drug at the right stage. Sci Transl Med. 2011;3(111):111 (2011).

Teunissen CE, Dijkstra C, Polman C. Biological markers in CSF and blood for axonal degeneration in multiple sclerosis. Lancet Neurol. 2005;4(1):32-41 (2005).

Tortelli R, Ruggieri M, Cortese R, et al. Elevated cerebrospinal fluid neurofilament light levels in patients with amyotrophic lateral sclerosis: a possible marker of disease severity and progression. Eur J Neurol. 2012;19(12):1561-1567 (2012).

Villemagne VL, Burnham S, Bourgeat P, et al. Amyloid β deposition, neurodegeneration, and cognitive decline in sporadic Alzheimer's disease: a prospective cohort study. Lancet Neurol. 2013;12(4):357-367 (2013).

Warren JD, Rohrer JD, Schott JM, Fox NC, Hardy J, Rossor MN. Molecular nexopathies: a new paradigm of neurodegenerative disease. Trends Neurosci. 2013;36(10):561-569 (2013).

Zetterberg H, Skillbäck T, Mattsson N, et al. Association of Cerebrospinal Fluid Neurofilament Light Concentration With Alzheimer Disease Progression. JAMA Neurol. 2016;73(1):60-67 (2016).

Zetterberg H, Wilson D, Andreasson U, et al. Plasma tau levels in Alzheimer's disease. Alzheimers Res Ther. 2013;5(2):9 (2013).

Chatterjee et al., "Association of Plasma Neurofilament Light Chain with Neocortical Amyloid-β Load and Cognitive Performance in Cognitively Normal Elderly Participants," J Alzheimer's Dis. 63(2):479-487 (2018).

Clark et al., "Plasma neurofilament light and phosphorylated tau 181 as biomarkers of Alzheimer's disease pathology and clinical disease progression," Alzheimer's Res Ther. 13(1):65 (2021).

Norgren et al., "Monoclonal antibodies selective for low molecular weight neurofilaments," Hybrid Hybridomics. 21(1):53-9 (2002).

Quiroz et al., "Plasma neurofilament light chain in the presenilin 1 E280A autosomal dominant Alzheimer's disease kindred: a cross-sectional and longitudinal cohort study," Lancet Neurol. 19(6):513-521 (2020).

"NF-light® (Neurofilament light) ELISA: Instructions for Use," IBL International GMBH. Ref. No. UD51001 (2015) (9 pages).

Ex parte Ambati (Appeal No. 2017-011580, U.S. Appl. No. 11/357,288, (PTAB 2019)).

"UmanDiagnostics NF-light™ Products," Quanterix™ The Science of Precision Health, <https://go.quanterix.com/l/228272/2021-10-07/2xlyld>, retrieved on Dec. 6, 2021 (4 pages).

"NF-light™ (Neurofilament light) ELISA CE-IVD," Quanterix, UmanDiagnostics, <https://www.quanterix.com/wp-content/uploads/2021/02/Uman_NFL_Elisa_CE_IVD-021621.pdf> (1 page).

Mattsson et al., "Association of Plasma Neurofilament Light With Neurodegeneration in Patients With Alzheimer Disease." JAMA Neurol. 74(5): 557-566 (Mar. 2017) (10 pages).

Benedet et al., "Stage-specific links between plasma neurofilament light and imaging biomarkers of Alzheimer's disease," Brain. 143(12):3793-3804 (Dec. 2020) (12 pages).

Preische et al., "Serum neurofilament dynamics predicts neurodegeneration and clinical progression in presymptomatic Alzheimer's disease," available in PMC Feb. 1, 2020, published in final edited form as: Nat Med. 25(2):277-283 (Feb. 2019) (27 pages).

Weston et al., "Longitudinal measurement of serum neurofilament light in presymptomatic familial Alzheimer's disease," Alzheimers REs Ther. 11(1):19 (Feb. 2019) (7 pages).

Sánchez-Valle et al., "Serum neurofilament light levels correlate with severity measures and neurodegeneration markers in autosomal dominant Alzheimer's disease," Alzheimers Res Ther. 10(1):113 (Nov. 2018) (6 pages).

Figure 4

|  | Non-carriers | Presymptomatic carriers | Symptomatic carriers |
|---|---|---|---|
| N | 11 | 19 | 18 |
| Age, years (SD) | 38.9 (9.5) | 36.0 (5.7) | 46.6 (9.3) |
| Gender, m/f | 3/8 | 10/9 | 13/5 |
| EYO (SD) | -5.4 (10.8) | -9.6 (5.5) | 3.4 (3.3) |
|  |  |  |  |
| MMSE /30 | 29.7 (0.6) | 29.2 (0.9) | 20.9 (6.7) |
| Global CDR | 0 | 0 | 0.78 (0.41) |
| CDR SOB | 0 | 0.1 (0.2) | 4.3 (3.3) |
| NART predicted IQ |  |  |  |
| WASI IQ |  |  |  |
| Estimated change in IQ | 9.1 (8.0) | 1.4 (9.2) | -13.2 (14.2) |
| Combined RMT average/50 | 45.7 (3.1) | 44.3 (3.4) | 37.2 (7.2) |
|  |  |  |  |
| Baseline brain volume (corrected for TIV), mL | 1234 (56) | 1221 (67) | 1108 (59) |
| Rate of change in brain volume, mL/year | -1.4 (4.2) | -1.4 (8.6) | -15.3 (8.5) |
| Baseline ventricular vol., (corrected for TIV), mL | 10.8 (5) | 13.6 (7.5) | 24.8 (9.2) |
| Rate of change in ventricular vol., mL/year | 0.1 (0.5) | 0.3 (1.2) | 4.3 (3.1) |
| Baseline hippocampal vol., mL |  |  |  |
| Rate of change in hippocampal vol., mL/year |  |  |  |
|  |  |  |  |
| Serum NfL, pg/mL | 12.7 (7.2) | 16.7 (7.7) | 46.0 (20.8) |

Figure 5

| Correlation between EYO and: | Spearman's R | p-value |
|---|---|---|
| Serum NfL | 0.73 | 0.005 |
| MMSE | 0.086 | 0.78 |
| CDR SOB | 0.51 | 0.073 |
| Change in IQ | -0.23 | 0.45 |
| Average RMT | 0.52 | 0.071 |
| Baseline brain volume, mL | -0.43 | 0.14 |
| Rate of change in brain volume, mL/year | 0.17 | 0.58 |
| Baseline ventricular vol., mL | 0.36 | 0.22 |
| Rate of change in ventricular vol., mL/year | 0.43 | 0.14 |

METHODS FOR DETECTING AN INDIVIDUAL AS BEING AT RISK OF DEVELOPING A NEURODEGENERATIVE DISEASE

The present invention relates to a method for detecting an individual as being at risk of developing a neurodegenerative disease, the method comprising a) measuring the amount or concentration of neurofilament-light (NfL) in a sample obtained from the individual; and b) detecting the individual as being at risk of developing the disease by comparing the amount or concentration determined in step (a) to the amount or concentration of NfL in a control, wherein an increased value of NfL relative to the control is indicative of the future development of the disease, as well as to uses related thereto.

In Alzheimer's disease pathological changes begin a number of years before the onset of clinical symptoms, with deposition of amyloid β (Aβ) and hyperphosphorylated tau followed by downstream neurodegeneration (Bateman R J, Xiong C, Benzinger T L, et al. Clinical and biomarker changes in dominantly inherited Alzheimer's disease. N Engl J Med 2012; 367:795-804; Villemagne V L, Burnham S, Bourgeat P, et al. Amyloid β deposition, neurodegeneration, and cognitive decline in sporadic Alzheimer's disease: a prospective cohort study. The Lancet Neurology 2013; 12:357-367). There is great interest in testing potential disease-modifying treatments for AD during this pre-symptomatic period, prior to clinically significant neuronal and loss (Sperling R A, Jack C R, Jr., Aisen P S. Testing the right target and right drug at the right stage. Sci Transl Med 2011; 3:111 cm133).

In order to facilitate this, robust and sensitive biomarkers are needed to identify at-risk individuals, stage their disease, and track disease progression (Sperling R A, Aisen P S, Beckett L A, et al. Toward defining the preclinical stages of Alzheimer's disease: recommendations from the National Institute on Aging-Alzheimer's Association workgroups on diagnostic guidelines for Alzheimer's disease. Alzheimers Dement 2011; 7:280-292). Ideally, any such biomarker should be non-invasive, inexpensive, and simple to acquire (Consensus report of the Working Group on: "Molecular and Biochemical Markers of Alzheimer's Disease". The Ronald and Nancy Reagan Research Institute of the Alzheimer's Association and the National Institute on Aging Working Group. Neurobiol Aging 1998; 19:109-116).

Detection of early AD pathogenic change has until now largely relied on either cerebrospinal fluid (CSF) analysis or neuroimaging techniques. Blood-based biomarkers of early AD disease activity would offer greater convenience and higher patient acceptability, but have proven more challenging than CSF measures for a number of reasons, including lower concentration of the target analyte making reliable detection and quantification more difficult. A recent systematic review identified no blood biomarkers that have utility in early disease (Olsson B, Lautner R, Andreasson U, et al. CSF and blood biomarkers for the diagnosis of Alzheimer's disease: a systematic review and meta-analysis. Lancet Neurol 2016; 15:673-684).

Neurofilament light (NfL) is a promising biomarker of neurodegeneration when sampled from CSF (Zetterberg H, Skillback T, Mattsson N, et al. Association of Cerebrospinal Fluid Neurofilament Light Concentration With Alzheimer Disease Progression. JAMA Neurol 2016; 73:60-67). Together with the neurofilament medium (NfM) and heavy (NfH) chains, NfL forms an important part of the structural integrity of axons (Lee M K, Xu Z, Wong P C, Cleveland D W. Neurofilaments are obligate heteropolymers in vivo. J Cell Biol 1993; 122:1337-1350).

Increased CSF NfL concentration is found in a number of neurological conditions, including AD, multiple sclerosis, motor neuron disease, frontotemporal dementia, and atypical parkinsonian disorders, and is thought to reflect axonal degeneration (Zetterberg H. et al., supra; Teunissen C E, Dijkstra C, Polman C. Biological markers in CSF and blood for axonal degeneration in multiple sclerosis. Lancet Neurol 2005; 4:32-41; Tortelli R, Ruggieri M, Cortese R, et al. Elevated cerebrospinal fluid neurofilament light levels in patients with amyotrophic lateral sclerosis: a possible marker of disease severity and progression. Eur J Neurol 2012; 19:1561-1567; Scherling C S, Hall T, Berisha F, et al. Cerebrospinal fluid neurofilament concentration reflects disease severity in frontotemporal degeneration. Ann Neurol 2014; 75:116-126; Hall S, Ohrfelt A, Constantinescu R, et al. Accuracy of a panel of 5 cerebrospinal fluid biomarkers in the differential diagnosis of patients with dementia and/or parkinsonian disorders. Arch Neurol 2012; 69:1445-1452).

In Alzheimer's disease (AD) sensitive biomarkers of early neurodegeneration are essential. A blood-based biomarker would be extremely valuable, but so far no such marker has been proven to discriminate early AD from healthy aging.

Therefore, there is a strong medical need for easily accessible biomarkers of AD neurodegeneration throughout both pre-symptomatic and symptomatic disease.

It was surprisingly found that measurement of serum neurofilament-light (NfL) provides a marker of early axonal degeneration and accordingly, an easily accessible biomarker of AD neurodegeneration throughout both pre-symptomatic and symptomatic disease. In particular, it was surprisingly found that measurement of serum neurofilament-light (NfL) provides an easily accessible biomarker of Alzheimer's Disease already in the pre-symptomatic phase of Alzheimer's Disease.

We here report the results of a study measuring serum NfL levels in a cohort of autosomal dominant familial AD (FAD) mutation carriers. Carriers of FAD mutations, in the presenilin 1 (PSEN1), presenilin 2 (PSEN2) or amyloid precursor protein (APP) genes, have relatively predictable ages at onset (Ryman D C, Acosta-Baena N, Aisen P S, et al. Symptom onset in autosomal dominant Alzheimer disease: a systematic review and meta-analysis. Neurology 2014; 83:253-260), which provides the opportunity for prospective study of asymptomatic individuals prior to the onset of clinical AD. FAD shares many features, both pathophysiologically and clinically, with the more common sporadic form of disease (Bateman R J, Aisen P S, De Strooper B, et al. Autosomal-dominant Alzheimer's disease: a review and proposal for the prevention of Alzheimer's disease. Alzheimers Res Ther 2011; 3:1). We assessed the ability of this method to detect pre-symptomatic rises in serum NfL in autosomal dominant familial AD (FAD).

NfL can be measured in serum using standard immunoassay formats (Gaiottino J, Norgren N, Dobson R, et al. Increased neurofilament light chain blood levels in neurodegenerative neurological diseases. PLOS One 2013; 8:e75091; Bacioglu M, Maia L F, Preische O, et al. Neurofilament Light Chain in Blood and CSF as Marker of Disease Progression in Mouse Models and in Neurodegenerative Diseases. Neuron 2016). Herein, we used a recently developed immunoassay based on the Single molecule array (SIMOA®) technique that allows quantification down to subfemtomolar concentrations (below 1 pg/ml) of the analyte (Rissin D M, Kan C W, Campbell T G, et al. Single-molecule enzyme-linked immunosorbent assay detects serum proteins at subfemtomolar concentrations. Nat Biotechnol 2010; 28:595-599). Serum NfL concentrations derived using this method correlate closely with CSF concentrations and are increased in HIV-associated dementia, progressive supranuclear palsy and frontotemporal dementia (Gisslen M. et al., EBioMedicine. 2015 Nov. 22; 3:135-40. doi: 10.1016/j.ebiom.2015.11.036. eCollection 2016; Rojas J. C. et al., Ann Clin Transl Neurol. 2016 Feb. 1; 3(3):216-25. doi: 10.1002/acn3.290. eCollection 2016; Rohrer J. D. et al., Neurology. 2016 Sep. 27; 87(13):1329-36. doi: 10.1212/WNL.0000000000003154).

We surprisingly found that elevated serum NfL are detectable prior to symptom onset, and correlate with disease stage and rate of decline in the pre-symptomatic and symptomatic participants of the study tested.

In particular, of the asymptomatic at-risk participants tested, 19 were mutation carriers (median EYO=8.3) and 11 non-carriers. Compared to non-carriers, correcting for age and gender, serum NfL was higher in both symptomatic mutation carriers (p<0.0001) and pre-symptomatic mutation carriers (p=0.007). Serum NfL correlated with EYO (p<0.0001) and multiple cognitive and imaging measures, including MMSE (p=0.0001) and whole-brain atrophy rate (p=0.0091).

It was concluded from the Examples that serum NfL concentration increased in FAD prior to symptom onset and correlated with measures of disease stage and severity. Serum NfL may thus be an easily accessible biomarker of early AD-related neurodegeneration.

Figure 6:
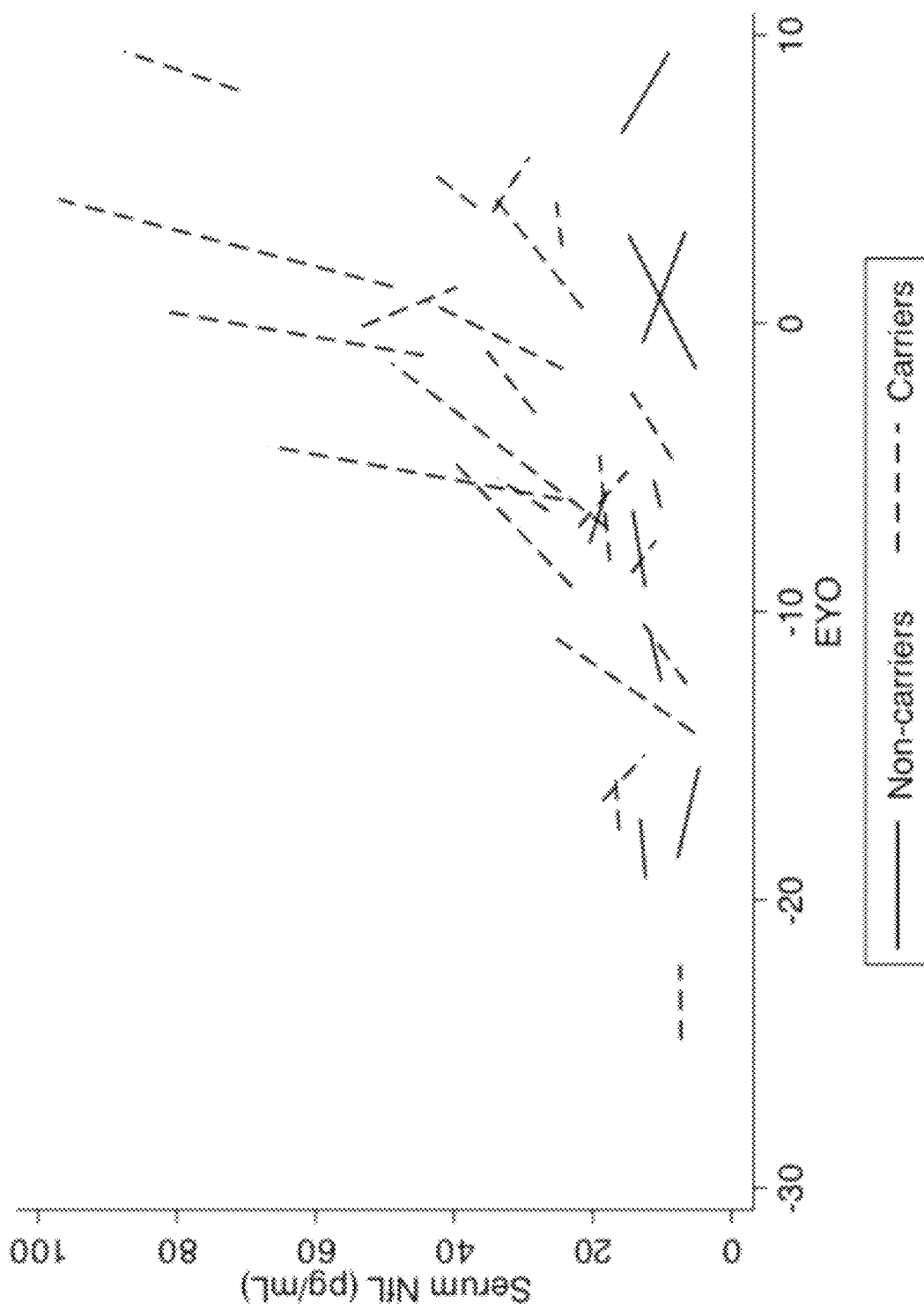

In particular, our study presents the first assessment of the utility of measuring serum NfL, using a new ultrasensitive assay, to detect early AD-related neurodegeneration. Our results in the Examples surprisingly show that serum NfL is elevated a number of years before the onset of clinical symptoms. We also show that serum NfL correlates very closely with number of years to/from estimated symptom onset. Therefore, serum NfL is able to track, and therefore monitor and predict, disease progression. Serum NfL is also found to correlate closely with current validated measures of AD severity, including structural imaging measures of atrophy and cognitive test scores. However, in the pre-symptomatic period, serum NfL may be more sensitive to neurodegenerative change than these more established measures. Longitudinal data show that serum NfL concentrations start to increase approximately 5 to 10 years prior to estimated years to symptom onset (EYO) in autosomal dominant familial AD (FAD) mutation carriers (FIG. 6).

Following our study provided in the Examples, it is now evident that serum NfL progressively rises over the 10 year period prior to the onset of symptomatic disease and correlates with other markers of neuronal loss. The current evidence therefore supports the use of serum NfL as an easily accessible biomarker of AD neurodegeneration throughout both pre-symptomatic and symptomatic disease.

Therefore, in one embodiment, the present invention relates to a method for detecting an individual as being at risk of developing a neurodegenerative disease, the method comprising
  a) measuring the amount or concentration of neurofilament-light (NfL) in a sample obtained from the individual; and
  b) detecting the individual as being at risk of developing the disease by comparing the amount or concentration determined in step (a) to the amount or concentration of NfL in a control,
wherein an increased value of NfL relative to the control is indicative of the future development of the disease.

The marker in the method of the invention is neurofilament light or NfL, preferably human neurofilament light or human NfL. Neurofilament light protein is a protein that in humans is encoded by the NEFL gene. Together with the neurofilament medium (NfM) and heavy (NfH) chains, NfL forms an important part of the structural integrity of axons. The human NfL protein has the sequence set forth in NCBI Reference Sequence No: NP_006149.2 as of Oct. 8, 2016. The human NfL mRNA has the sequence set forth in GenBank Accession No: BC066952.1 as of Oct. 8, 2016. The steps of measuring the amount or concentration of neurofilament-light (NfL) protein includes measuring the amount or concentration of the full-length protein, a fragment thereof, which is representative and specific for the full length protein, a modified form of NfL such as a phosphorylated NfL, or a aggregate of NfL proteins such as a dimer, a oligomer or a higher order aggregate in the sample, particularly a blood sample.

The method of the invention is for detecting an individual as being at risk of developing a neurodegenerative disease.

An individual being at risk of developing a neurodegenerative disease encompasses individuals in the clinical phase or symptomatic individuals, in particular individuals in the early phase, of said neurodegenerative disease and individuals in the pre-clinical phase of said neurodegenerative disease or pre-symptomatic individuals. Individuals in the pre-clinical phase do not exhibit at least one clinical symptom of said neurodegenerative disease and/or are not suspected to suffer from said neurodegenerative disease. Individuals in the clinical phase exhibit at least one clinical symptom of said neurodegenerative disease and/or are suspected to suffer from said neurodegenerative disease.

A neurodegenerative disease is understood as a disease of the central and peripheral nervous system characterized by the progressive loss of structure or function of neurons, including death of neurons. Neurodegenerative diseases include Parkinson's disease, Alzheimer's disease (AD), amyotrophic lateral sclerosis (ALS), denervation atrophy, otosclerosis, dementia, such as vascular dementia, dementia with Lewy bodies (DLB), dementia associated with Parkinson's disease, frontotemporal dementia, Creutzfeldt-Jakob disease, Normal pressure hydrocephalus dementia, Wernicke-Korsakoff Syndrome and AD, multiple sclerosis, Huntington's disease, encephalopathy associated with acquired immunodeficiency disease (AIDS), and other diseases associated with neuronal cell toxicity and cell death. In the examples, it was shown that serum NfL can be used as an easily accessible biomarker of AD neurodegeneration throughout both pre-symptomatic and symptomatic disease. Therefore, Alzheimer's disease or AD represents a preferred neurodegenerative disease.

Alzheimer's disease or AD is a chronic neurodegenerative disease of the central nervous system associated with progressive memory loss, resulting in dementia. Two pathological characteristics are observed in AD patients at autopsy: extracellular plaques and intracellular tangles in the hippocampus, cerebral cortex, and other areas of the brain essential for cognitive function. Plaques are formed mostly from the deposition of amyloid beta (An), a peptide derived from amyloid precursor protein (APP). Filamentous tangles are formed from paired helical filaments composed of neurofilament and hyperphosphorylated tau protein, a microtubule-associated protein. There are different stages of AD. For assessing Alzheimer's disease, one or more of the following tests may be combined: brain magnetic resonance imaging (MRI), neurological examination and cognitive assessment. Such tests are described in the examples. Further, clinical AD stages may be differentiated by persons skilled in the art pursuant to the CDR classification for assessing cognitive impairment. The CDR classification (Clinical Dementia Rating) differentiates the following stages: 0=Normal; 0.5=Very Mild Dementia, corresponding to MCI; 1=Mild Dementia, corresponding to mild AD; 2=Moderate Dementia, corresponding to moderate AD; 3=Severe Dementia, corresponding to severe AD. MRI may be used for determining whole brain or ventricular volumes.

The main clinical feature and symptom of AD is a progressive cognitive decline, and accordingly, cognitive impairment, such as memory loss. Symptoms of Alzheimer's disease include cognitive impairment, including language impairment, deficits in visual function, memory loss, and impairment of short-term memory, increased anxiety, sleeping disorder, personality changes, such as progressive passivity or marked agitation, decreased expressions of affection, depression and psychosis. The memory dysfunction involves impairment of learning new information which is often characterized as short-term memory loss. In the early and moderate stages of the illness, recall of remote well-learned material may appear to be preserved, but new information cannot be adequately incorporated into memory. Disorientation to time is closely related to memory disturbance. Language impairments are also a prominent symptom of AD. These are often manifest first as word finding difficulty in spontaneous speech. The language of the AD patient is often vague, lacking in specifics and may have increased automatic phrases and cliché s. Difficulty in naming everyday objects is often prominent. Complex deficits in visual function are present in many AD patients, as are other focal cognitive deficits such as apraxia, acalculia and left-right disorientation. Impairments of judgment and problems solving are frequently seen. Non-cognitive or behavioral symptoms are also common in AD and may account for an event larger proportion of caregiver burden or stress than the cognitive dysfunction. Personality changes are commonly reported and range from progressive passivity to marked agitation. Patients may exhibit changes such as decreased expressions of affection. Depressive symptoms are present in up to 40%. A similar rate for anxiety has also been recognized. Psychosis occurs in 25%. In some cases, personality changes may predate cognitive abnormality.

Accordingly, a "symptom of Alzheimer's disease" is understood to include cognitive impairment, including language impairment, deficits in visual function, memory loss, and impairment of short-term memory, increased anxiety, sleeping disorder, personality changes, such as progressive passivity or marked agitation, decreased expressions of affection, depression and psychosis. An early symptom of Alzheimer's disease is mild cognitive impairment (MCI). Mild cognitive impairment or MCI is understood by a skilled person as grey area between intact cognitive functioning and clinical dementia as defined in the "Diagnostic and Statistical Manual for Mental Disorders" (DSM), in particular as defined in version DSM-5. About 70% of patients exhibiting mild cognitive impairment (MCI) later develop Alzheimer's disease. The remaining patients develop different forms of dementia, such as vascular dementia.

When applying the method of the invention, an increased value of NfL relative to the control is indicative of the future development of the disease.

The future development encompasses cases wherein the individual is pre-symptomatic at the time point of obtaining the sample. In case an increased value of NfL relative to the control is determined, the individual will likely develop the neurodegenerative disease in future, such as in about 1 month, 6 months, 1, 2, 3, 4, 5, 6, 7, 8, 9, 10, 11, 12, 13, 14 or 15 years. In these cases, the onset of the neurodegenerative disease is detected about 1 month, 6 months, 1, 2, 3, 4, 5, 6, 7, 8, 9, 10, 11, 12, 13, 14 or 15 years prior to the onset of one or more symptoms of the neurodegenerative disease. In one preferred embodiment, the individual is determined to likely develop the neurodegenerative disease in about one year or more, preferably about two years or more, more preferably about three years or more, still more preferably about four years or more, most preferably about five years or more. In these cases the onset of the neurodegenerative disease is detected about at least one year, preferably at least two years, more preferably at least three years, still more preferably four years, most preferably at least five years prior to the onset of one or more symptoms of the neurodegenerative disease. In the Examples, the serum NfL levels were increased and were further correlated with the estimated years to symptom onset (EYO) for pre-symptomatic FAD mutation carriers.

Further, the future development encompasses cases wherein the individual is symptomatic at the time point of obtaining the sample. In case an increased value of NfL relative to the control is determined, the individual will likely further develop the neurodegenerative disease in future and/or exhibit disease progression. For example, in case an individual exhibits mild cognitive impairment (MCI) at the time point of obtaining the sample, and an increased value of NfL relative to the control is determined, the individual will likely show disease progression, such as progression of cognitive impairment, and/or onset of one or more further symptoms of Alzheimer's disease or other forms of dementia.

Therefore, in a preferred embodiment of the present invention, the individual is pre-symptomatic or symptomatic.

A symptomatic individual is understood as an individual who exhibits at least one clinical symptom of the neurodegenerative disease. In case of Alzheimer's disease, a symptomatic individual may for example exhibit dementia or cognitive impairment, such as mild cognatic impairment.

A pre-symptomatic individual is understood as an individual who does not exhibit a clinical symptom of a neurodegenerative disease. Such individual may be a healthy individual, or an individual suffering from disease(s) different from a neurodegenerative disease, or individuals where FAD cases occurred in the family, but who do not show AD symptoms.

In a preferred embodiment, the invention relates to a method for detecting a pre-symptomatic human individual as being at risk of developing Alzheimer's disease, the method comprising
  a) measuring the amount or concentration of neurofilament-light (NfL) protein in a blood sample obtained from the individual; and
  b) detecting the individual as being at risk of developing Alzheimer's disease by comparing the amount or concentration determined in step (a) to the amount or concentration of NfL protein in a control, wherein an increased value of NfL protein relative to the control is indicative of the future development of Alzheimer's disease.

More preferably,
  the amount or concentration of NfL protein correlates with the time to onset of one or more symptoms of Alzheimer's disease, preferably wherein the amount or concentration of NfL protein is elevated before the onset of clinical symptoms, and/or the method is capable of detecting the onset of Alzheimer's disease at least one year, preferably at least two years, more preferably at least three years, still more preferably four years, most preferably at least five years, prior to the onset of one or more symptoms, especially wherein the amount or concentration of NfL protein is elevated before the onset of clinical symptoms, and/or the method is capable of detecting the onset of Alzheimer's disease at least one year, preferably at least two years, more preferably at least three years, still more preferably four years, most preferably at least five years, prior to the onset of one or more symptoms, preferably wherein the amount or concentration of NfL protein is elevated before the onset of clinical symptoms, and/or the Alzheimer's disease is familial Alzheimer's disease, and/or the method is repeated at different times in order to monitor the individual or a prophylactic treatment, and/or the control value is obtained from a healthy control individual or a healthy control cohort, or from the same individual at an earlier time point, and/or the blood sample is serum, plasma, or whole blood, preferably serum; and/or an increased value of NfL protein relative to the control is indicative of the development of Alzheimer's disease in about 1 month to 10 years.

As indicated above, it was surprisingly found in the Examples, that the serum NfL levels were increased for pre-symptomatic FAD mutation carriers and that they were further correlated with the estimated years to symptom onset (EYO) for such pre-symptomatic FAD mutation carriers. It was in particular found that for pre-symptomatic FAD mutation carriers with more estimated years to symptom onset (EYO), less increased values of NfL were determined as compared to pre-symptomatic FAD mutation carriers with less estimated years to symptom onset (EYO).

For FAD mutation carriers, the estimated years to symptom onset (EYO) can be determined from the family history, as indicated above. The EYO value relates to the time at which the pre-symptomatic individual is predicted to show clinical symptoms of AD. For FAD mutation carriers, the EYO value is correlating with the time to onset of one or more symptoms of the disease.

Accordingly, in another preferred embodiment of the present invention, the amount or concentration of NfL correlates with the time to onset of one or more symptoms of the disease. The time to onset of a disease relates to the time period passing until a pre-symptomatic individual at a certain time point of investigation, will exhibit at least one clinical symptom of the disease in question and/or exhibits the disease in question. The time to onset of the neurodegenerative disease, in particular AD, may for example be 1 month, 6 months, 1, 2, 3, 4, 5, 6, 7, 8, 9, 10, 11, 12, 13, 14 or 15 years. Therefore, the method of the invention is capable of detecting the onset of the neurodegenerative disease, in particular of AD, 1 month, 6 months, 1, 2, 3, 4, 5, 6, 7, 8, 9, 10, 11, 12, 13, 14 or 15 years prior to the onset of one or more symptoms of the neurodegenerative disease, in particular of AD.

Accordingly, in yet another preferred embodiment of the present invention, the method is capable of detecting the onset of the disease at least one year, preferably at least two years, more preferably at least three years, still more preferably four years, most preferably at least five years, prior to the onset of one or more symptoms.

In another preferred embodiment of the present invention, the neurodegenerative disease is Alzheimer's disease, particularly familial Alzheimer's disease.

In the Examples, elevated NfL levels were identified in both symptomatic and pre-symptomatic mutation carriers for Familial Alzheimer's disease; the pre-symptomatic individuals being on average nine years from predicted symptom onset. Therefore, the method of the invention is in particular useful for detecting an individual as being at risk of developing Familial Alzheimer's disease (FAD).

Familial Alzheimer's disease or FAD is a form of Alzheimer's disease that is inherited in an autosomal dominant fashion. Familial Alzheimer's disease usually strikes earlier in life, typically as before the age of 65, usually between 50 and 65 years of age, but can be as early as 15. Autosomal dominant familial AD (FAD) mutation carriers exhibit an increased risk of developing Alzheimer's disease. FAD mutations include mutations in the presenilin 1 (PSEN1), presenilin 2 (PSEN2) and amyloid precursor protein (APP) genes.

The future development of the neurodegenerative disease is to be detected in an individual.

The individual according to the present invention may be any human or non-human animal, especially a mammal, fish, reptile or bird. Thus, the methods and compositions described herein are applicable to both human and veterinary disease. Evidently, non-human mammals of particular interest include laboratory animals, such as rodents, including e.g. mouse, rat, rabbit, or zebrafish, domestic animals, such as pets, and animals of commercial value, including e.g. guinea pig, rabbit, horse, donkey, cow, sheep, goat, pig, chicken, camel, cat, dog, turtle, tortoise, snake, lizard or goldfish.

In a preferred embodiment of the present invention, the individual is a human.

In order to detect the future development of the neurodegenerative disease, a sample is obtained from the individual.

The sample may be any sample suitable for measuring the marker NfL according to the present invention and refers to a biological sample obtained for the purpose of evaluation in vitro. It comprises material which can be specifically related to the individual and from which specific information about the individual can be determined, calculated or inferred. A sample can be composed in whole or in part of biological material from the patient (e.g. a blood sample). A sample can also be material that has contacted the patient in a way that allows tests to be conducted on the sample which provides information about the individual. The sample may preferably comprise any body fluid. Exemplary test samples include blood, serum, plasma, urine, saliva, whole blood, or particles circulating in peripheral blood, such as exosomes, or cerebrospinal fluid (CSF). The sample may be taken from the individual and used immediately or processed before the measuring step a). Processing may include purification (e.g. separation such as centrifugation), concentration, dilution, lysis of cellular components, freezing, acidification, conservation etc. Preferred samples are serum, plasma, whole blood, or particles circulating in peripheral blood, such as exosomes, with serum representing the most preferred type of sample.

Particles circulating in peripheral blood are particles which can be separated from peripheral blood by centrifugation protocols. A particularly preferred particle circulating in peripheral blood is an exosome. Exosomes are small vesicles in the diameter range of about 30 to about 100 nm, which are of endocytic origin, and which are released in the extra-cellular milieu by several cell types. Exosomes can be isolated and/or separated from peripheral blood samples by methods known to a skilled person, e.g. by ultracentrifugation, in particular differential ultracentrifugation, optionally in combination with micro-filtration or a gradient, or size-exclusion chromatography, or commercially available kits, such as Exoquick® (SBI, Palo Alto, USA).

Therefore, in another preferred embodiment of the present invention, the sample is cerebrospinal fluid or a blood sample, preferably serum, plasma, whole blood, or particles circulating in peripheral blood, such as exosomes, more preferably serum.

In accordance with the present invention, the amount or concentration of marker NfL is determined in order to detect an individual as being at risk of developing a neurodegenerative disease. The amount of a substance is a standards-defined quantity that measures the size of an ensemble of elementary entities, such as atoms, molecules, electrons, and other particles. It is sometimes referred to as chemical amount. The International System of Units (SI) defines the amount of substance to be proportional to the number of elementary entities present. The SI unit for amount of substance is the mole. It has the unit symbol mol. The concentration of a substance is the amount of a constituent divided by the total volume of a mixture. Several types of mathematical description can be distinguished: mass concentration, molar concentration, number concentration, and volume concentration. The term concentration can be applied to any kind of chemical mixture, but most frequently it refers to solutes and solvents in solutions. The molar (amount) concentration has variants such as normal concentration and osmotic concentration.

The step of measuring the level of the marker NfL may be carried out as follows: The sample and optionally calibrator and/or control may be contacted with a specific binding agent for NfL, which is optionally immobilized, e.g. on a solid phase, under conditions allowing the binding of the agent to the marker NfL. Optionally, unbound binding agent is removed by a separation step (e.g. one or more washing steps). A second agent (e.g. a labeled agent) may be added to detect the bound binding agent and/or the bound marker NfL, to allow binding to and quantification of the same. Optionally, unbound second agent is removed by a second separation step (e.g. one or more washing steps). The amount of the second binding agent, which is proportional to the amount of the marker, may be quantified, e.g. based on the label. Quantification may be based on e.g. a calibration curve constructed for each assay by plotting measured value versus the concentration for each calibrator. The concentration or amount of marker in the sample may be then read from the calibration curve.

After the amount or concentration of the marker is determined, the value obtained is compared to the amount or concentration of the marker NfL as established in a control (e.g. a control sample or control cohort or control population or a control group). The expression "comparing the amount or concentration . . . to the amount or concentration . . . in a control" is merely used to further illustrate what is obvious to the skilled artisan anyway. The control sample may be an internal or an external control. In one embodiment an internal control is used, i.e. the marker level is assessed in the test sample as well as in one or more other sample taken from the same subject to determine if there are any changes in the level of said marker. Therefore, in one preferred embodiment, the control value is obtained from the same individual at an earlier time point. It is further preferred for a control, that the same individual is pre-symptomatic at said earlier time point or exhibits few and/or mild disease symptoms at said earlier time point. In another embodiment an external control is used. For an external control, the presence or amount of the marker in a sample derived from the individual is compared to its amount or concentration in an individual or population of individuals known to be free of a given condition (e.g. the neurodegenerative disease or risk of developing the neurodegenerative disease, such as AD), i.e., "normal individual". Therefore, in one preferred embodiment, control value is obtained from a healthy control individual or a healthy control cohort. Usually, the sample's marker level is directly or indirectly correlated with a diagnosis or prediction and the marker level is e.g. used to determine whether an individual is at risk of developing a neurodegenerative disease. It is within the skills of the practitioner to choose an appropriate control sample/population/cohort/group and a control or reference value for the marker established therein. It will be appreciated by the skilled artisan that such control, in one preferred embodiment, is obtained from a reference population that is age-matched and free of confounding diseases. As also clear to the skilled artisan, the absolute marker values established in a control will be dependent on the assay used. Preferably, samples from 100 or more well-characterized individuals from the appropriate reference population are used to establish a control (reference) value. Also preferred is that the reference population may be chosen to consist of at least 20, 30, 50, 200, 500 or 1000 individuals. Healthy individuals represent a preferred reference population for establishing a reference. Alternatively, reference populations may be used in methods of the invention, e.g. one population of healthy individuals and one population of individuals known to be symptomatic of a neurodegenerative disease, such as AD, or mutation carriers of FAD.

Therefore, in another preferred embodiment of the present invention, the control value is obtained from a healthy control individual or a healthy control cohort, or from the same individual at an earlier time point.

In the sample, the amount or concentration of the marker molecule NfL is measured. A variety of methods for measuring the marker molecule NfL are known in the art and any of these can be used.

Preferably, the marker NfL is specifically measured from a liquid sample by use of a specific binding agent.

A specific binding agent is, e.g., a receptor for the marker or an antibody to the marker or a nucleic acid complementary to the nucleic acid relating to the marker protein (e.g. a nucleic acid complementary to a marker's mRNA or relevant part thereof). Preferably, the marker molecule NfL is measured at the protein level.

Therefore, in another preferred embodiment of the present invention, NfL is measured as NfL protein or NfL mRNA.

NfL mRNA can be detected by any technique known in the art. These include Northern blot analysis, reverse transcriptase-PCR amplification (RT-PCR), microarray analysis and RNAse protection.

For example, NfL mRNA in a sample can be measured in a Northern blot assay. Here, tissue RNA is fractionated by electrophoresis, fixed to a solid membrane support, such as nitrocellulose or nylon, and hybridized to a probe capable of selectively hybridizing with NfL mRNA in the sample. The actual levels may be quantitated by reference to one or more control housekeeping genes.

Housekeeping genes are genes which are involved in the general metabolism or maintenance of the cell, and are considered to be expressed at a constant level irrespective of cell type, physiological state or stage in the cell cycle. Examples of suitable housekeeping genes are beta actin, GAPDH, histone H3.3 or ribosomal protein L13.

In another embodiment, the NfL mRNA is amplified and quantitatively assayed. The polymerase chain reaction (PCR) procedure can be used to amplify specific nucleic acid sequences through a series of iterative steps including denaturation, annealing of oligonucleotide primers designed according to the nfl mRNA sequence, and extension of the primers with DNA polymerase. In reverse transcriptase-PCR (RT-PCR), this procedure is preceded by a reverse transcription step to allow a large amplification of the number of copies of mRNA.

Quantitation of RT-PCR products can be done while the reaction products are building up exponentially, and can generate diagnostically useful clinical data. In one embodiment, the measurement is carried out by reference to one or more housekeeping genes which are also amplified by RT-PCR. Quantitation of a RT-PCR product may be undertaken, for example, by gel electrophoresis visual inspection or image analysis, HPLC or by use of fluorescent detection methods.

In one more preferred embodiment, NfL is measured as NfL protein.

Determination of proteins as binding partners of a marker protein can be performed using any of a number of known methods for identifying and obtaining proteins that specifically interact with proteins, for example, a yeast two-hybrid screening system such as that described in U.S. Pat. Nos. 5,283,173 and 5,468,614, or the equivalent. A specific binding agent has preferably at least an affinity of $10^7$ l/mol for its corresponding target molecule. The specific binding agent preferably has an affinity of $10^8$ l/mol or even more preferred of $10^9$ l/mol for its target molecule. As the skilled artisan will appreciate, the term specific is used to indicate that other biomolecules present in the sample do not significantly bind to the binding agent specific for the marker. Preferably, the level of binding to a biomolecule other than the target molecule results in a binding affinity which is only 10% or less, more preferably only 5% or less of the affinity to the target molecule, respectively. A preferred specific binding agent will fulfill both the above minimum criteria for affinity as well as for specificity.

Preferably, a specific binding agent is an antibody reactive with the marker NfL. The term antibody refers to a polyclonal antibody, a monoclonal antibody, antigen binding fragments of such antibodies, single chain antibodies as well as to genetic constructs comprising the binding domain of an antibody.

Preferably, the marker is detected in an immunoassay, in particular in a sandwich type assay format. In such assay, a first specific binding agent (e.g. a first antibody) is used to capture the marker in question. Optionally, the first specific binding agent is either covalently or non-covalently, in particular passively, bound to a solid phase. The solid phase is typically glass, a magnetic or paramagnetic material or a polymer, the most commonly used polymers being cellulose, polyacrylamide, nylon, polystyrene, polyvinyl chloride, or polypropylene. The solid phase may be in the form of microparticles, tubes, beads, discs of microplates, or any other surface suitable for conducting an immunoassay. The binding processes are well-known in the art and encompass cross-linking, covalently binding and physically adsorbing, the binding agent, to form a complex of first specific binding agent and solid support, e.g. a polymer-antibody complex. Non-covalent binding may be achieved, e.g. by bioaffine binding pairs, such as biotin and streptavidin.

After a suitable time period of incubation with the marker, i.e. a period of time sufficient to allow formation of a complex of the marker and the first specific binding agent, under suitable conditions, and after an optional washing step, a second specific binding agent (e.g. a second antibody), which is labeled to be directly or indirectly detectable, is used to capture either the marker in question, or the first specific binding agent, or the formed complex comprising the marker and the first specific binding agent. The second specific binding agent may contain a detectable reporter moiety or label such as an enzyme, dye, radionuclide, luminescent group, fluorescent group or biotin, or the like. Any reporter moiety or label could be used with the methods disclosed herein as long as the signal of such is directly related or proportional to the quantity of binding agent. Any unreacted material may be washed away. The amount of the second binding agent that remains bound to either the marker in question, or the first specific binding agent, or the formed complex comprising the marker and the first specific binding agent is then determined using a method appropriate for the specific detectable reporter moiety or label. For radioactive groups, scintillation counting or autoradiographic methods are generally appropriate. Antibody-enzyme conjugates can be prepared using a variety of coupling techniques (for review see, e.g., Scouten, W. H., Methods in Enzymology 135:30-65, 1987). Spectroscopic methods can be used to detect dyes (including, for example, colorimetric products of enzyme reactions), luminescent groups and fluorescent groups. Biotin can be detected using avidin or streptavidin, coupled to a different reporter group (commonly a radioactive or fluorescent group or an enzyme). Enzyme reporter groups can generally be detected by the addition of substrate (generally for a specific period of time), followed by spectroscopic, spectrophotometric or other analysis of the reaction products. Standards and standard additions can be used to determine the level of antigen in a sample, using well known techniques.

The term "antibodies" includes polyclonal antibodies, monoclonal antibodies, antigen-binding fragments thereof, as well as any naturally occurring or recombinantly produced binding partners, which are molecules that specifically bind a NfL protein. The term "antigen-binding fragments" of an antibody refers to molecules which possess the ability to bind to an antigen in a similar fashion as an antibody but which is smaller in size than a complete antibody molecule. Exemplified, two "antigen binding fragments" of an antibody are obtained by papain digestion which produces three fragments, namely two identical fragments, called "Fab fragments" (also referred to as "Fab portion" or "Fab region") each with a single antigen binding site, and a residual "Fc fragment" (also referred to as "Fc portion" or "Fc region") whose name reflects its ability to crystallize readily. Further antigen-binding fragments include "Fab' fragment" which refer to a Fab fragment additionally comprise the hinge region of an Ig molecule, and "F(ab')$_2$ fragments" which are understood to comprise two Fab' fragments being either chemically linked or connected via a disulfide bond. Whilst "single domain antibodies (sdAb)" (Desmyter et al. (1996) Nat. Structure Biol. 3:803-811). Further encompassed are "Nanobodies" which only comprise a single VH domain, "single chain Fv (scFv)" fragments comprise the heavy chain variable domain joined via a short linker peptide to the light chain variable domain (Huston et al. (1988) Proc. Natl. Acad. Sci. USA 85, 5879-5883), divalent single-chain variable fragments (discFvs) which can be engineered by linking two scFvs (scFvA-scFvB). This can be done by producing a single peptide chain with two VH and two VL regions, yielding "tandem scFvs" (VHA-VLA-VHB-VLB). Another possibility is the creation of scFvs with linkers that are too short for the two variable regions to fold together, forcing scFvs to dimerize. Usually linkers with a length of 5 residues are used to generate these dimers. This type is known as "diabodies". Still shorter linkers (one or two amino acids) between a VH and VL domain lead to the formation of monospecific trimers, so-called "triabodies" or "tribodies". Bispecific diabodies are formed by expressing to chains with the arrangement VHA-VLB and VHB-VLA or VLA-VHB and VLB-VHA, respectively. Single chain diabodies (scDb) comprise a VHA-VLB and a VHB-VLA fragment which are linked by a linker peptide (P) of 12-20 amino acids, preferably 14 amino acids, (VHA-VLB-P-VHB-VLA). Dual affinity retargeting molecules ("DART" molecules) are diabodies additionally stabilized through a C-terminal disulfide bridge.

Antibodies are generated by state of the art procedures, e.g., as described in Tijssen (Tijssen, P., Practice and theory of enzyme immunoassays, Elsevier Science Publishers B. V., Amsterdam (1990), the whole book, especially pages 43-78). In addition, the skilled artisan is well aware of methods based on immunosorbents that can be used for the specific isolation of antibodies. By these means the quality of polyclonal antibodies and hence their performance in immunoassays can be enhanced (Tijssen, P., supra, pages 108-115).

For the achievements as disclosed in the present invention, polyclonal antibodies raised in e.g. goats may be used. However, clearly also polyclonal antibodies from different species, e.g., rats, rabbits or guinea pigs, as well as monoclonal antibodies can be used. Since monoclonal antibodies can be produced in any amount required with constant properties, they represent ideal tools in development of an assay for clinical routine.

For measurement, the sample obtained from an individual is incubated with the specific binding agent for the marker in question under conditions appropriate for formation of a binding agent marker-complex. Such conditions need not be specified, since the skilled artisan without any inventive effort can easily identify such appropriate incubation conditions. The amount of binding agent marker-complex is measured and used in the methods and uses of the invention. As the skilled artisan will appreciate there are numerous methods to measure the amount of the specific binding agent marker-complex all described in detail in relevant textbooks (cf., e.g., Tijssen P., supra, or Diamandis, E. P. and Christopoulos, T. K. (eds.), Immunoassay, Academic Press, Boston (1996)). In the Examples, the monoclonal antibodies mAB47:3 and mAb2:1 contained in the NF-Light assay from Uman Diagnostics (UmanDiagnostics, Umea, Sweden) were successfully used for measuring the amount and concentration of NfL protein in the samples.

Particularly, monoclonal antibodies to the marker NfL protein are used in a quantitative (amount or concentration of the marker is determined) immunoassay.

Preferred immunoassays which can be used in the present invention include Enzyme Linked Immunosorbent Assay (ELISA), electrochemical assay (ECL), electrochemiluminescent immunoassay (ECLIA), radioimmunoassay (RIA) or ultra-sensitive single molecule array assay (SIMOA®).

As described above, there are a variety of methods for measuring NfL protein. Commercially available products for measuring NfL include an NfL ELISA (NF-Light assay from Uman Diagnostics (UmanDiagnostics, Umea, Sweden)). Further, an electro-chemiluminescence assay described in the prior art may be used for measuring NfL protein (Kuhle J, Barro C, Andreasson U, et al. Comparison of three analytical platforms for quantification of the neurofilament light chain in blood samples: ELISA, electrochemiluminescence immunoassay and Simoa. Clin Chem Lab Med 2016).

In particular embodiments of measuring the amount or concentration of NfL in a sample, the first and second specific binding agent, preferably first and second antibody, are mixed with the sample comprising the marker to be analyzed.

In a preferred embodiment, the first specific binding agent, which is preferably an antibody, is coated onto microparticles or beads, more preferably on paramagnetic microparticles or beads. Further, the second specific binding agent, which is preferably an antibody, is labeled to be directly or indirectly detectable.

In one preferred embodiment, the coating onto microparticles or beads may be achieved by bioaffine binding pairs, such as biotin and streptavidin. In such embodiment, the microparticle or bead is in a preferred embodiment a magnetic or paramagnetic microparticle or bead.

In one preferred embodiment, wherein the immunoassay is performed without a washing step, such mixing and incubating is performed in a single reaction vessel. The sequence of adding and mixing the three ingredients (e.g. microparticles coated with first specific binding agent, such as antibody, sample comprising the marker, second detectably-labeled antibody, respectively) is not critical. This mixture is incubated for a period of time sufficient for the first specific binding agent (in particular the first antibody coated onto the microparticles or beads) and the detectably labeled second specific binding agent (in particular the second antibody), to bind to NfL.

In another preferred embodiment, wherein the immuno assay is performed with a washing step, the adding and mixing of the first specific agent (in particular the first antibody coated onto microparticles or beads), sample and detectably-labeled second specific binding agent, such as an antibody, is performed sequentially into a single reaction vessel. In a first step (the analyte-capturing step), microparticles or beads coated with the first antibody are incubated with the sample to be analyzed for a period of time sufficient for the analyte, i.e. NfL, to be bound. Following a washing step, the detectably-labeled second antibody is added and incubated for a period of time sufficient for the second antibody to bind to the analyte, i.e. NfL. In a preferred embodiment, the method is practiced in a competitive assay format.

In a preferred embodiment, the mixture comprising the first specific agent (in particular the first antibody coated onto microparticles or beads), sample and detectably-labeled second specific binding agent, such as an antibody, is incubated for less than 60 min, i.e. less than 60, 55, 50, 45, 40, 35, 30, 25, 20, 15, 10, or 5 min. In more preferred embodiments, the mixture is incubated for 4 min to 1 hour (i.e. 4, 5, 6, 7, 8, 9, 10, 15, 20, 25, 30, 35, 40, 45, 50, 55, or 60 min). In even more preferred embodiments, the mixture is incubated for 5 min to 45 min, i.e. for 5, 6, 7, 8, 9, 10, 15, 20, 25, 30, 35, 40, or 45 min. In further more preferred embodiments, the mixture is incubated for 5 min to 30 min, i.e. for 5, 6, 7, 8, 9, 10, 15, 20, 25, or 30 min. In particularly preferred embodiments, the mixture is incubated for 9 or 18 min. In yet another preferred embodiment, the mixture is incubated for 1-12 hours (i.e. 1, 2, 3, 4, 5, 6, 7, 8, 9, 10, 11, or 12 hours). In more preferred embodiments, the mixture is incubated for 1-4 hours or for 8-12 hours.

In further preferred embodiments, the mixture is incubated at a temperature of 3-40° C. (i.e. 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40° C.). In a preferred embodiment, the mixture is incubated at a temperature of 3° C. to 8° C. (i.e. 3, 4, 5, 6, 7 or 8° C.), more preferably at 4-5° C., or at a temperature of 20° C. to 25° C. (i.e. at 20, 21, 22, 23, 24, or 25° C.), in particular at a temperature of 20-22° C., or at a temperature of 35-37° C.

It is well-known to the person skilled in the art that incubation temperature and incubation time depend upon each other. Accordingly, in preferred embodiments, the mixture is incubated at 20-25° C. for 10 min to 1 hours, i.e. the mixture is incubated at 20, 21, 22, 23, 24, or 25° C. for 10, 15, 20, 25, 30, 35, 40, 45, 50, 55, or 60 min. In other preferred embodiments, the mixture is incubated for less than 10 min or less than 20 min at 22° C. In yet other preferred embodiments, the mixture is incubated for 1-12 hours at 3-8° C. In particular, the mixture is incubated for 1-4 hours or for 8-12 hours at 3-8° C., in particular at 4-5° C.

The first specific agent and/or second specific binding agent, preferably, first and/or the second antibody, are incubated for a period of time sufficient for the first antibody coated onto the microparticles or beads and the detectably labeled second antibody, to bind to NfL in the sample.

In a preferred embodiment, first specific agent and/or second specific binding agent, preferably the first and/or the second antibody, is/are comprised in and/or are incubated in a physiological solution, in particular in a physiological buffer. In a preferred embodiment, the buffer is selected from the group of TAPS, Bicine, Tris, Tricine, TAPSO, HEPES, TES, MOPS, PIPES, Cacodylate, and MES. In a more preferred embodiment, the buffer is a MES buffer. In an even more preferred embodiment, the MES buffer comprises the following components: 50 mM MES, 150 mM NaCl, 2 mM EDTA-$Na_2$ (dihydrate), 0.1% N-Methylisothiazolon-HCl, 0.1% Oxypyrion, 0.1% Polydocanol (Thesit), 1.0% Albumin RPLA 4 assay quality, 0.2% PAK↔R-IgG (DET), Millipore-water, pH adjusted to 6.30 with 2N NaOH.

In one preferred embodiment, the formed first specific binding agent-marker-second specific binding agent complex, preferably the first antibody-antigen (marker)-second antibody complex, in particular the complex formed comprising the first antibody, NfL—the second antibody, is detected via any method well-known in the art. In particular embodiments, the complex formed is detected via electrochemiluminescence, chemiluminescence, or fluorescence.

In an electrochemical (ECL) or electrochemiluminescent (ECLIA) assay, a bound analyte molecule is detected by a label linked to a detecting agent. An electrode electrochemically initiates luminescence of a chemical label linked to a detecting agent. Light emitted by the label is measured by a photodetector and indicates the presence or quantity of bound analyte molecule/target molecule complexes. ECLIA methods are described, for example, in U.S. Pat. Nos. 5,543,112; 5,935,779; and 6,316,607. Signal modulation can be maximized for different analyte molecule concentrations for precise and sensitive measurements. For example, the label may be a ruthenium label.

In further embodiments, an ultra-sensitive single molecule array (SIMOA®) sandwich immunoassay is performed. It is described in the prior art that NfL can be measured in serum using standard immunoassay formats, but control samples and many of the samples from the disease groups will have NfL concentrations below the analytical sensitivity of the methods. In the Examples, a recently developed immunoassay based on the Single molecule array (SIMOA®) technique was successfully used, that allows quantification down to subfemtomolar concentrations (below 1 pg/ml) of the analyte, and which is 25-fold as sensitive as the previous electrochemiluminescence-based method for NfL. In the Examples the SIMOA® assay as described in Rissin D. M. et al. (Nature Biotechnology (doi:10.1038/nbt.1641)) was used successfully.

During ultra-sensitive single molecule array (SIMOA®) sandwich immunoassays, fluorescently distinct paramagnetic beads, which may have a diameter of about 2.7 µm diameter, are coupled with a capture antibody. A conventional bead-based sandwich immunoassay approach is applied wherein single immunocomplexes labeled with an enzyme, in particular streptavidin-β-galactosidase, are formed on the bead surface. When samples containing extremely low concentrations of analytes are tested, the ratio of analyte molecules, as well as of the resulting immunocomplexes to beads is small (<1) and the percentage of beads that contain a labeled immunocomplex follows a Poisson distribution. Accordingly, beads carry either a single immunocomplex or none. The very low concentrations of enzyme labels on the bead surface can be detected by loading the beads into an array of a high number of wells, such as >$10^4$ or >$10^5$ wells, e.g. 216,000 wells, and confining the fluorophores generated by individual enzymes to extremely small volumes, such as about 50 femtoliter. Beads are sealed with oil to ensure only one bead in a well. Beads carrying a single enzyme-labeled immunocomplex generate a high local concentration of fluorophores in the confined well. By acquiring time-lapsed fluorescence images of the array using standard microscopic optics, it is possible to differentiate beads associated with a single enzyme molecule ("on" well) from those not associated with an enzyme molecule ("off" well). At low concentrations of proteins, when the ratio of enzyme labels to beads is less than about 1.2, beads carry either zero or low numbers of enzymes, and protein concentration is quantified by counting the presence of "on" or "off" beads (i.e. a digital regime). At higher protein concentrations, each bead typically carries multiple enzyme labels, and the average number of enzyme labels present on each bead is quantified from a measure of the average fluorescence intensity (i.e. an analog regime). Both the digital and analog concentration ranges are quantified by a common unit, namely, average number of enzyme labels per bead (AEB). By combining digital and analog mode for fluorescence measurement of singulated beads, a linear dynamic range of over 6 orders of magnitude to enzyme label can be achieved.

In accordance with the present invention, an increased value for the amount or concentration of the marker relative to the control is indicative of the future development of the neurodegenerative disease. If the value is increased, the neurodegenerative disease will develop in future. The individual identified thereby may be subject to further diagnostic or therapeutic methods, including further blood or CSF tests, imaging methods, cognitive tests or therapy, in particular preventive therapy. The skilled practitioner will be able to select suitable means in accordance with the medical practice of the prevailing country.

In one embodiment, the value is increased if the value amount is increased by at least 110%, more preferably by at least 120%, more preferably by at least 130%, more preferably by at least 140%, more preferably by at least 150%, more preferably by at least 160%, more preferably by at least 170%, more preferably by at least 180%, even more preferably by at least 190% relative to the control value.

Alternatively, the value for NFL as measured in a control group or a control population are for example used to establish a cut-off value or a reference range. A value above such cut-off value or out-side the reference range and its higher end is considered as increased. In a one embodiment a fixed cut-off value is established. Such cut-off value is chosen to match the diagnostic or predictive question of interest. In one embodiment, the value for NfL as measured in a control group or a control population is used to establish a reference range. In a preferred embodiment an NfL concentration is considered as increased if the value measured is above the 90%-percentile of the reference range. In further preferred embodiments a value for NfL is considered as increased if the value measured is above the 95%-percentile, the 96%-percentile, the 97%-percentile or the 97.5%-percentile of the reference range. A cut-off value may represent an appropriate value to distinguish an individual at risk of developing a neurodegenerative disease from an individual not at risk of developing a neurodegenerative disease.

A suitable cut-off value may be chosen depending on the sensitivity and specificity desired. Sensitivity and specificity are statistical measures of the performance of a binary classification test, also known in statistics as classification function:

Sensitivity (also called the true positive rate) measures the proportion of positives that are correctly identified as such (e.g., the percentage of people at risk of developing a neurodegenerative disease who are correctly identified as having the risk).

Specificity (also called the true negative rate) measures the proportion of negatives that are correctly identified as such (e.g., the percentage of people not at risk of developing a neurodegenerative disease who are correctly identified as not having the risk).

For any test, there is usually a trade-off between the measures. For instance, in an airport security setting in which one is testing for potential threats to safety, scanners may be set to trigger on low-risk items like belt buckles and keys (low specificity), in order to reduce the risk of missing objects that do pose a threat to the aircraft and those aboard (high sensitivity). This trade-off can be represented graphically as a receiver operating characteristic curve. A perfect predictor would be described as 100% sensitive (e.g., all individuals at risk are identified as individuals at risk) and 100% specific (e.g., all healthy are not identified as individuals at risk); however, theoretically any predictor will possess a minimum error bound known as the Bayes error rate. The cut-off can be set in order to either increase sensitivity or specificity.

In statistics, a receiver operating characteristic (ROC), or ROC curve, is a graphical plot that illustrates the performance of a binary classifier system as its discrimination threshold is varied. The curve is created by plotting the true positive rate (TPR) against the false positive rate (FPR) at various threshold settings. As detailed above, the true-positive rate is also known as sensitivity or the sensitivity index d', known as "d-prime" in signal detection and biomedical informatics, or recall in machine learning. The false-positive rate is also known as the fall-out and can be calculated as (1−specificity). The ROC curve compares sensitivity versus specificity across a range of values for the ability to predictor a dichotomous outcome. The area under the curve (AUC presents the overall accuracy for comparing test performance (Florkowski C M, 2008, Clin Biochem Rev 29 (Suppl 1): S83-S87). Sensitivity is the ability of a test to correctly classify an individual as diseased. The ability of a test to correctly classify an individual as disease- or risk-free is called specificity.

ROC analysis provides tools to select possibly optimal models and to discard suboptimal ones independently from (and prior to specifying) the cost context or the class distribution. ROC analysis is related in a direct and natural way to cost/benefit analysis of diagnostic decision making.

In yet another preferred embodiment of the present invention, the method is repeated at different times in order to monitor the individual or a prophylactic treatment.

The method can be repeated at 1, 2, 3, 4, 5, 6, 7, 8, 9, 10 or more different times. Thereby, a time course can be established, which allows for monitoring the individual. The time intervals may differ, and, for example, may be a time interval between 1 day and 20 years, such as between 1 month and 1, 2, 3, 4, 5, 6, 7, 8, 9, or 10 years. Also, the time intervals may differ in case the method is repeated 2, 3, 4, 5, 6, 7, 8, 9, 10 or more different times. For example, the control may be a healthy control individual or a healthy control cohort, or may be from the same individual at a respective earlier time point, such as from the same individual at the first time point. In case an increase in value of NfL is determined over time, the risk of developing the neurodegenerative disease further increases, whereas a constant or decreased value at a later time point indicates that the risk of developing the neurodegenerative disease does not further increase, or decreases.

Accordingly, in another embodiment, the present invention relates to a method for detecting an individual as being at risk of developing a neurodegenerative disease, the method comprising a) contacting (i) a sample obtained from the individual, and (ii) a first specific binding agent for NfL, whereby a complex comprising NfL and the first specific binding agent is formed, b) optionally separating the complex comprising NfL and the first specific binding agent for NfL from the remaining sample, c) contacting the complex comprising NfL and the first specific binding agent for NfL with a second specific binding agent for NfL, whereby a complex comprising NfL and the second specific binding agent for NfL, and/or the first specific binding agent for NfL is formed, d) measuring the amount or concentration of the complex comprising NfL, and the first specific binding agent and/or the second specific binding agent; and e) detecting the individual as being at risk of developing the disease by comparing the amount or concentration determined in step (d) to the amount or concentration of a complex comprising NfL and the second specific binding agent, and/or the first specific binding agent in a control, wherein an increased value of the complex comprising NfL and the second specific binding agent and/or the first specific binding agent relative to the control is indicative of the future development of the disease.

As described above with regard to the first embodiment of the present invention, a quantitative sandwich immunoassay may be used to determine the amount or concentration of NfL protein. For example, a first specific NfL antibody as preferred specific binding agents may be incubated with sample obtained from the individual in step (a). Thereby, a complex comprising NfL and the first NfL antibody is formed. The first specific NfL antibody is preferably bound to a solid support or is capable of binding to a solid support. Such solid support may for example be a well, such as a multiwall plate, an array, such as a microarray or nanoarray, or a bead or microparticle, such as a magnetic bead or microparticle or paramagnetic bead or microparticle. The binding to the support, e.g. by covalent or non-covalent linkage, allows for separating the complex comprising NfL and the first specific binding agent for NfL according to step (b) from the remaining sample. Alternatively or in addition, one or more washing steps may be included for separating from the remaining sample. A non-covalent linkage may be achieved by members of bioaffine binding pairs, such as, for example, biotin and streptavidin, or receptor and ligand. Subsequently, the complex is incubated with a second specific binding agent for NfL, such as a second NfL antibody. Thereby, a complex comprising NfL and the second specific binding agent for NfL, and/or the first specific binding agent for NfL, is formed. The complex formed also depends on the epitopes bound by the specific binding agents, respectively. In one preferred embodiment, the second specific binding agent for NfL and the first specific binding agent for NfL bind to distinct, more preferably non-overlapping, epitopes of the NfL protein, allowing for complex formation comprising both specific binding agents and detection in a sandwich immunoassay format. In one preferred embodiment, the second specific binding agent for NfL is labeled to be directly or indirectly detectable, as described above, thereby allowing detecting the amount or concentration of the complex comprising NfL and the second specific binding agent for NfL, and/or the first specific binding agent. An increased value of the complex comprising NfL and the second specific binding agent for NfL, and/or the first specific binding agent relative to the control is indicative of the future development of the neurodegenerative disease, as described above.

Preferably, the invention relates to an in vitro method for detecting a pre-symptomatic human individual as being at risk of developing Alzheimer's disease, the method comprising a) contacting (i) a blood sample obtained from the individual, and (ii) a first specific binding agent for NfL protein, whereby a complex comprising NfL protein and the first specific binding agent is formed, b) optionally separating the complex comprising NfL and the first specific binding agent for NfL from the remaining sample, c) contacting the complex comprising NfL protein and the first specific binding agent for NfL protein with a second specific binding agent for NfL protein, whereby a complex comprising NfL protein, and the second specific binding agent for NfL protein, and/or the first specific binding agent for NfL protein is formed, d) measuring the amount or concentration of the complex comprising NfL protein and the first specific binding agent and/or the second specific binding agent; and e) detecting the individual as being at risk of developing Alzheimer's disease by comparing the amount or concentration determined in step (d) to the amount or concentration of a complex comprising NfL and the second specific binding agent, and/or the first specific binding agent in a control, wherein an increased value of the complex comprising NfL protein and the second specific binding agent, and/or the first specific binding agent relative to the control is indicative of the future development of Alzheimer's disease.

In another preferred embodiment of the present invention, NfL is measured as NfL mRNA.

NfL mRNA can be detected by any technique known in the art. These include Northern blot analysis, reverse transcriptase-PCR amplification (RT-PCR), microarray analysis and RNAse protection.

For example, NfL mRNA in a sample can be measured in a Northern blot assay. Here, tissue RNA is fractionated by electrophoresis, fixed to a solid membrane support, such as nitrocellulose or nylon, and hybridized to a probe capable of selectively hybridizing with NfL mRNA in the sample. The actual levels may be quantitated by reference to one or more control housekeeping genes. Housekeeping genes are genes which are involved in the general metabolism or maintenance of the cell, and are considered to be expressed at a constant level irrespective of cell type, physiological state or stage in the cell cycle. Examples of suitable housekeeping genes are beta actin, GAPDH, histone H3.3 or ribosomal protein L13.

In another embodiment, the NfL mRNA is amplified and quantitatively assayed. The polymerase chain reaction (PCR) procedure can be used to amplify specific nucleic acid sequences through a series of iterative steps including denaturation, annealing of oligonucleotide primers designed according to the nfl mRNA sequence, and extension of the primers with DNA polymerase. In reverse transcriptase-PCR (RT-PCR), this procedure is preceded by a reverse transcription step to allow a large amplification of the number of copies of mRNA.

Quantitation of RT-PCR products can be done while the reaction products are building up exponentially, and can generate diagnostically useful clinical data. In one embodiment, the measurement is carried out by reference to one or more housekeeping genes which are also amplified by RT-PCR. Quantitation of a RT-PCR product may be undertaken, for example, by gel electrophoresis visual inspection or image analysis, HPLC or by use of fluorescent detection methods.

In accordance with the present invention, an increased value for the amount or concentration of the marker relative to the control is indicative of the future development of the neurodegenerative disease. If the value is increased, the neurodegenerative disease will develop in future. The individual identified thereby may be subject to further diagnostic or therapeutic methods, including further blood or CSF tests, imaging methods, cognitive tests or therapy, in particular preventive therapy. The skilled practitioner will be able to select suitable means in accordance with the medical practice of the prevailing country.

In one embodiment, the value is increased if the value amount is increased by at least 110%, more preferably by at least 120%, more preferably by at least 130%, more preferably by at least 140%, more preferably by at least 150%, more preferably by at least 160%, more preferably by at least 170%, more preferably by at least 180%, even more preferably by at least 190% relative to the control value.

Alternatively, the value for NFL as measured in a control group or a control population are for example used to establish a cut-off value or a reference range. A value above such cut-off value or out-side the reference range and its higher end is considered as increased. In a one embodiment a fixed cut-off value is established. Such cut-off value is chosen to match the diagnostic or predictive question of interest. In one embodiment, the value for NfL as measured in a control group or a control population is used to establish a reference range. In a preferred embodiment an NfL concentration is considered as increased if the value measured is above the 90%-percentile of the reference range. In further preferred embodiments a value for NfL is considered as increased if the value measured is above the 95%-percentile, the 96%-percentile, the 97%-percentile or the 97.5%-percentile of the reference range. A cut-off value may represent an appropriate value to distinguish an individual at risk of developing a neurodegenerative disease from an individual not at risk of developing a neurodegenerative disease.

A suitable cut-off value may be chosen depending on the sensitivity and specificity desired. Sensitivity and specificity are statistical measures of the performance of a binary classification test, also known in statistics as classification function:

Sensitivity (also called the true positive rate) measures the proportion of positives that are correctly identified as such (e.g., the percentage of people at risk of developing a neurodegenerative disease who are correctly identified as having the risk).

Specificity (also called the true negative rate) measures the proportion of negatives that are correctly identified as such (e.g., the percentage of people not at risk of developing a neurodegenerative disease who are correctly identified as not having the risk).

For any test, there is usually a trade-off between the measures. For instance, in an airport security setting in which one is testing for potential threats to safety, scanners may be set to trigger on low-risk items like belt buckles and keys (low specificity), in order to reduce the risk of missing objects that do pose a threat to the aircraft and those aboard (high sensitivity). This trade-off can be represented graphically as a receiver operating characteristic curve. A perfect predictor would be described as 100% sensitive (e.g., all individuals at risk are identified as individuals at risk) and 100% specific (e.g., all healthy are not identified as individuals at risk); however, theoretically any predictor will possess a minimum error bound known as the Bayes error rate. The cut-off can be set in order to either increase sensitivity or specificity.

In statistics, a receiver operating characteristic (ROC), or ROC curve, is a graphical plot that illustrates the performance of a binary classifier system as its discrimination threshold is varied. The curve is created by plotting the true positive rate (TPR) against the false positive rate (FPR) at various threshold settings. As detailed above, the true-positive rate is also known as sensitivity or the sensitivity index d', known as "d-prime" in signal detection and biomedical informatics, or recall in machine learning. The false-positive rate is also known as the fall-out and can be calculated as (1−specificity). The ROC curve compares sensitivity versus specificity across a range of values for the ability to predictor a dichotomous outcome. The area under the curve (AUC presents the overall accuracy for comparing test performance (Florkowski C M, 2008, Clin Biochem Rev 29 (Suppl 1): S83-S87). Sensitivity is the ability of a test to correctly classify an individual as diseased. The ability of a test to correctly classify an individual as disease- or risk-free is called specificity.

ROC analysis provides tools to select possibly optimal models and to discard suboptimal ones independently from (and prior to specifying) the cost context or the class distribution. ROC analysis is related in a direct and natural way to cost/benefit analysis of diagnostic decision making.

In yet another preferred embodiment of the present invention, the method is repeated at different times in order to monitor the individual or a prophylactic treatment.

The method can be repeated at 1, 2, 3, 4, 5, 6, 7, 8, 9, 10 or more different times. Thereby, a time course can be established, which allows for monitoring the individual. The time intervals may differ, and, for example, may be a time interval between 1 day and 20 years, such as between 1 month and 1, 2, 3, 4, 5, 6, 7, 8, 9, or 10 years. Also, the time intervals may differ in case the method is repeated 2, 3, 4, 5, 6, 7, 8, 9, 10 or more different times. For example, the control may be a healthy control individual or a healthy control cohort, or may be from the same individual at a respective earlier time point, such as from the same individual at the first time point. In case an increase in value of NfL is determined over time, the risk of developing the neurodegenerative disease further increases, whereas a constant or decreased value at a later time point indicates that the risk of developing the neurodegenerative disease does not further increase, or decreases.

In case the patient receives a prophylactic treatment, such as treatment with a therapeutically effective amount of anti-A beta oligomer antibody, such as aducanumab, or a cognitive enhancer, such as memantine, the method can be used to monitor prophylactic treatment. In case an increase in value of NfL is determined over time, the risk of developing the neurodegenerative disease further increases, indicating that the prophylactic treatment is not successful, whereas a constant or decreased value indicates that the risk of developing the neurodegenerative disease does not further increase or decreases, indicating that the prophylactic treatment is successful.

As shown in the Examples, NfL can surprisingly be used for detecting an individual as being at risk of developing a neurodegenerative disease. In particular, an increased value of NfL in a sample obtained from the individual relative to a control is indicative of the future development of the disease.

Therefore, in another embodiment, the present invention relates to the use of NfL for detecting an individual as being at risk of developing a neurodegenerative disease, wherein an increased value of NfL in a sample obtained from the individual relative to a control is indicative of the future development of the disease. The use is preferably an in vitro use.

In a preferred embodiment, the use is further defined as specified for the methods of the present invention. Accordingly, the embodiments disclosed herein for a method of the present invention also apply to the use of the present invention. In particular, Alzheimer's disease is a preferred neurodegenerative disease.

Preferably, the invention relates to the use of NfL protein for detecting a human pre-symptomatic individual as being at risk of developing Alzheimer's disease, wherein an increased value of NfL protein in a blood sample obtained from the individual relative to a control is indicative of the future development of Alzheimer's disease, especially wherein the use is further defined as specified above in the context of the methods of the invention.

The marker NfL can further aid a physician in detecting an individual as being at risk of developing a neurodegenerative disease.

Therefore, in a yet further embodiment, the present invention relates to a method for aiding in detecting an individual as being at risk of developing a neurodegenerative disease comprising
  a) receiving a sample,
  b) measuring the amount or concentration of neurofilament-light (NfL) in said sample; and
  c) providing information on the amount or concentration of NfL determined in step (b) to a physician, thereby aiding in detecting an individual as being at risk of developing a neurodegenerative disease.

In particular, a biochemical laboratory, a physician, trained laboratory personnel, or an automated analysis system can receive a sample of the individual to be tested in step a), such as a cerebrospinal fluid or a blood sample, preferably serum, plasma, whole blood, or particles circulating in peripheral blood, such as exosomes, more preferably serum. Such sample may be received by delivery to the laboratory, physician, trained laboratory personnel, or the automated analysis system, such as by manual or automated transfer, courier or postal delivery. Typically, the sample is received in a suitable container, such as an optionally sealed vessel or syringe. The sample received in step a) may be unprocessed or processed. A processed sample includes a sample obtainable after purification (e.g. separation such as centrifugation), concentration, dilution, lysis of cellular components, freezing, acidification, conservation etc. Preferred samples are serum, plasma, whole blood, or particles circulating in peripheral blood, such as exosomes, with serum representing the most preferred type of sample. For example, the received sample may be cooled and/or frozen prior to step b).

Subsequently, the amount or concentration of neurofilament-light (NfL) is measured in said sample, as described in detail above.

The information on the amount or concentration of NfL determined in step (b) is subsequently provided to a physician. Providing the information may be achieved by any means suitable for such purpose, such as, for example, by electronic, written, visual and/or oral means. For example, the information on the amount or concentration may be provided electronically, e.g. via e-mail or by delivery of an electronic storage medium containing the information stored thereon. Further, a written report containing in the information or presentation visually providing the information may be delivered. Further, the information may be provided orally, e.g. on the phone. Thereby, the information provided aids the physician in detecting an individual as being at risk of developing a neurodegenerative disease. For example, in case the physician finds that the amount or concentration of NfL is an increased relative to a control, the physician will identify the patient as being at risk of developing the disease is indicative of the future development of the disease. The physician can adequately choose an appropriate control, as described above. For example, the information on the control value may be obtained from a healthy control individual or a healthy control cohort, or from the same individual at an earlier time point. As the amount or concentration of NfL correlates with the time to onset of one or more symptoms of the disease, the physician can determine the time to onset of one or more symptoms of the disease when obtaining the information in step c). In particular, the method is capable of detecting the onset of the disease at least one year, preferably at least two years, more preferably at least three years, still more preferably four years, most preferably at least five years, prior to the onset of one or more symptoms. In a preferred embodiment, the neurodegenerative disease is Alzheimer's disease, particularly familial Alzheimer's disease.

In a preferred embodiment, the method is further defined as specified for the method for detecting an individual as being at risk of developing a neurodegenerative disease of the present invention.

Accordingly, the embodiments disclosed herein for a method for detecting an individual as being at risk of developing a neurodegenerative disease of the present invention also apply to the method for aiding in detecting an individual as being at risk of developing a neurodegenerative disease of the present invention.

Preferably, the present invention relates to a method for aiding in detecting a pre-symptomatic human individual as being at risk of developing Alzheimer's disease comprising
a) receiving a blood sample,
b) measuring the amount or concentration of neurofilament-light (NfL) protein in said sample; and
c) providing information on the amount or concentration of NfL protein determined in step b) to a physician, thereby aiding in detecting an individual as being at risk of developing Alzheimer's disease,
especially wherein the method is further defined as specified above in the context of the methods of the invention.

In a yet further embodiment, the present invention relates to a method for preventing and/or treating a neurodegenerative disorder in an individual, the method comprising
i) detecting an individual as being at risk of developing a neurodegenerative disease, comprising the steps:
a) measuring the amount or concentration of neurofilament-light (NfL) in a sample obtained from the individual; and
b) detecting the individual as being at risk of developing the disease by comparing the amount or concentration determined in step (a) to the amount or concentration of NfL in a control,
wherein an increased value of NfL relative to the control is indicative of the future development of the disease,
ii) administering a therapy and/or preventive therapy to the individual, in case the individual is identified as being at risk of developing the disease in step i).

For example, a therapeutically effective amount of agent suitable for prevention or therapy of the disease may be administered to the patient. For example, an effective amount for therapy or prevention of an anti-A beta oligomer antibody, such as aducanumab, or a cognitive enhancer, such as memantine, may be administered to an individual identified as being at risk of developing AD by a method of the present invention. The skilled person is aware of therapeutically effective doses and dosage regiments as well as formulations for such agents. For example, memantine may be formulated as tablets or drops. Further, about 1 mg to 50 mg, such as 20 mg, memantine may be administered per day. Further, agents suitable for prevention or therapy of other neurodegenerative diseases are known to a skilled person.

In a preferred embodiment, the method is further defined as specified for the further methods of the present invention. Accordingly, the embodiments disclosed herein for a method for detecting an individual as being at risk of developing a neurodegenerative disease of the invention also apply to the method for preventing and/or treating a neurodegenerative disorder of the present invention. In particular, Alzheimer's disease is a preferred neurodegenerative disease.

In general, the disclosure is not limited to the particular methodology, protocols, and reagents described herein because they may vary. Further, the terminology used herein is for the purpose of describing particular embodiments only and is not intended to limit the scope of the present disclosure. As used herein and in the appended claims, the singular forms "a", "an", and "the" include plural reference unless the context clearly dictates otherwise. Similarly, the words "comprise", "contain" and "encompass" are to be interpreted inclusively rather than exclusively.

Unless defined otherwise, all technical and scientific terms and any acronyms used herein have the same meanings as commonly understood by one of ordinary skill in the art in the field of the disclosure. Although any methods and materials similar or equivalent to those described herein can be used in the practice as presented herein, the specific methods, and materials are described herein.

The term "about" in the context of a value refers to the value±10%, preferably the value±5%.

FIGURES AND TABLES

FIG. 1: Box and whisker plots for serum NfL across the three groups.

Figure 2:
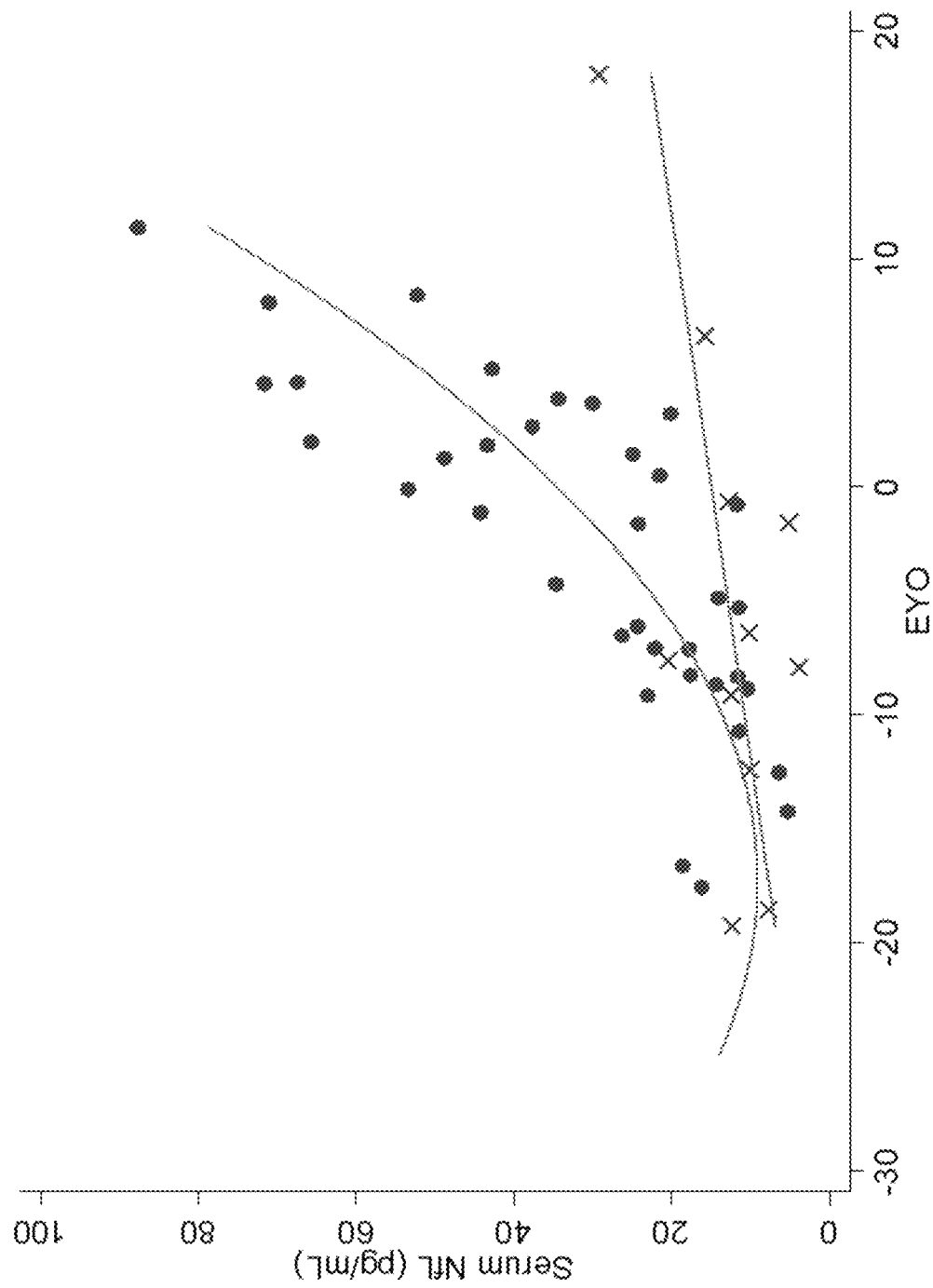

FIG. 2: Scatter plot of serum NfL against EYO. Mutation carriers are represented by dots, and non-carriers by crosses. Unadjusted regression lines are fitted. Any individual participants who it may be possible to identify, and therefore determine their mutation status, have been removed from the graph to ensure genetic blinding is maintained (but regression lines take in to account all participants including those not shown). •: Mutation carriers. x: Non-carriers.

Figure 3:
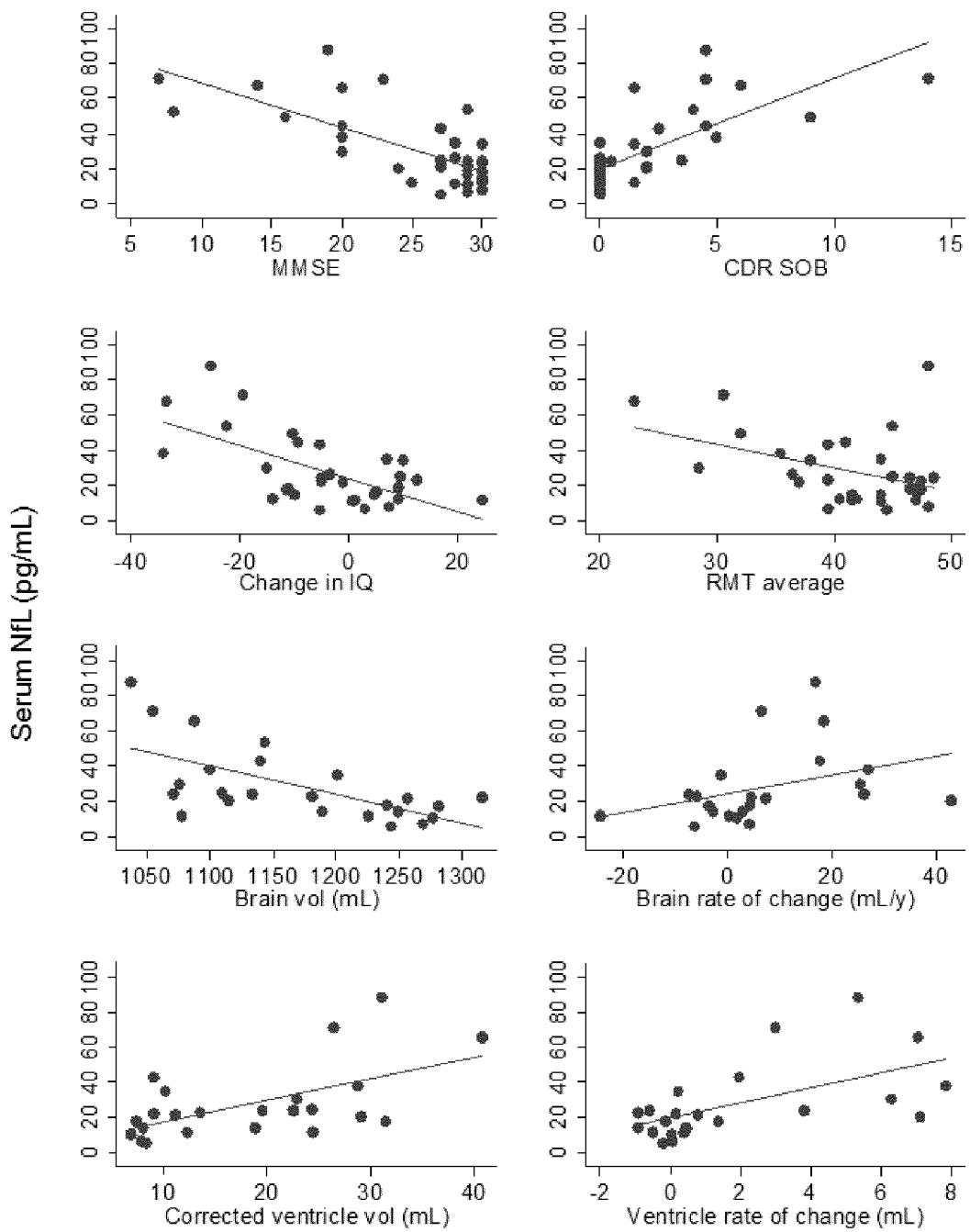

FIG. 3: Scatter plots of serum NfL against cognitive and imaging measures. Unadjusted regression lines are fitted.

FIG. 4: Table 1: Participant demographics, cognitive test scores, imaging measures and serum NfL concentration. All values are group means (with SD). Measures are uncorrected for any covariables.

FIG. 5: Table 2: Pre-symptomatic correlations between biomarkers and EYO. Spearman correlation coefficients for serum NfL, cognitive test scores, and imaging measures against EYO, in pre-symptomatic participants only. To allow for direct comparisons between the different measures, only the 13 pre-symptomatic mutation carriers for whom imaging measures were available are included.

FIG. 6: Longitudinal data from 32 of the subjects described in Table 1. These subjects (mutation carriers represented by dotted lines and non-mutation carriers by solid lines) were sampled at two time points. The time between the two sampling time points is indicated by the length of the line. Serum NfL concentrations start to increase approximately 5 to 10 years prior to estimated years to symptom onset (EYO) in autosomal dominant familial AD (FAD) mutation carriers.

EXAMPLES

Methods

Forty-eight individuals from families affected by genetic mutations in either PSEN1 or APP were recruited. Eighteen participants had symptomatic familial AD, and 30 were asymptomatic but at 50% risk of developing symptomatic disease in the future. For each participant, serum NfL was measured using an ultrasensitive immunoassay on the Single molecule array (SIMOA®) platform. Structural MRI and a number of cognitive measures were also performed. Thirty-three individuals had a second MRI scan (mean interval±SD=1.33±0.46 years), allowing rates of atrophy to be calculated. Genetic testing was performed to deduce the presence or absence of a mutation. A generalised least squares regression model was used to compare serum NfL between symptomatic mutation carriers, pre-symptomatic mutation carriers and non-carriers. Spearman correlation coefficients assessed associations between serum NfL and 1) estimated years to symptom onset (EYO), 2) cognitive measures, and 3) imaging measures of brain atrophy.

Study Design and Participants

We recruited forty-eight participants from FAD families between 2010 and 2015 to a biomarker study of FAD at the Dementia Research Centre, University College London. Eighteen participants had symptomatic FAD, with pathogenic mutations in either the PSEN1 or APP genes; 30 individuals were asymptomatic but, by virtue of having an affected parent, were at 50% risk of developing symptomatic disease in the future. For all participants, genetic testing was performed to determine the presence or absence of a mutation. Genetic data were provided only to designated individuals performing the statistical analysis, thus ensuring that the participants, the clinicians assessing them, and those performing the laboratory analysis remained blind to their genetic status.

Each participant underwent blood sampling, brain magnetic resonance imaging (MRI), neurological examination, and cognitive assessment, with all assessments completed within four months of blood sample collection. The cognitive assessment included the Wechsler Abbreviated Scale of Intelligence (WASI) (Wechsler D. WASI: Wechsler abbreviated scale of intelligence. Hove: Psychological Corporation, 1999), the National Adult Reading Test (NART) (a measure of predicted premorbid IQ), Recognition Memory Test (RMT) for Faces and Words, the Mini-Mental State Examination (MMSE). All individuals identified a close informant who was interviewed separately to gain a collateral history. The Clinical Dementia Rating Scale (CDR), which incorporates information from both the participant and the informant, was used to provide an additional estimate of clinical severity. Both global CDR and CDR sum of boxes (SOB) were calculated. Individuals were defined as symptomatic if the global CDR was >0 and consistent symptoms of cognitive decline were reported by the participant and/or their informant. Estimated years to symptom onset (EYO) was calculated for the mutation carriers by subtracting the participant's current age from the age at which their affected parent first developed progressive cognitive symptoms.

Measurement of Serum NfL Concentrations

Serum samples were collected from each participant and then processed, aliquoted and frozen at −80° C. according to standardized procedures. Serum NfL concentrations were measured using the NF-Light assay from Uman Diagnostics (UmanDiagnostics, Umea, Sweden), transferred onto the SIMOA® platform employing a homebrew kit (Quanterix Corp, Boston, MA, USA) and detailed instructions can be found in the SIMOA® Homebrew Assay Development Guide (Quanterix). In short, paramagnetic carboxylated beads (Cat #: 100451, Quanterix) were activated by adding 5% (v/v) 10 mg/mL 1-ethyl-3-(3-dimethylaminopropyl) carbodiimide (EDAC, Cat #: 100022, Quanterix) to a magnetic beads solution with $1·4×10^6$ beads/µl. Following a 30 min incubation at room temperature (RT) the beads were washed using a magnetic separator and an initial volume, i.e., EDAC+bead solution volumes in the previous step, of 0.3 mg/mL ice cold solution of the capture antibody (UD1, UmanDiagnostics) was added. After 2 h incubation on a mixer (2000 rpm, Multi-Tube Vortexer, Allsheng, China) at RT the beads were washed and an initial reaction volume of blocking solution was added. After three washes the conjugated beads were suspended and stored at 4° C. pending analysis. Prior to analysis the beads were diluted to 2500 beads/µl in bead diluent. The detection antibody (1 mg/mL, UD2, UmanDiagnostics) was biotinylated by adding 3% (v/v) 3.4 mM EZ-Link™ NHS-PEG4-Biotin (Quanterix) followed by 30 min incubation at RT. Free biotin was removed using spin filtration (Amicon® Ultra-2, 50 kD, Sigma) and the biotinylated antibody was stored at 4° C. pending analysis. The serum samples were assayed in duplicate on a SIMOA® HD-1 instrument (Quanterix) using a 2-step Assay Dilution protocol that starts with an aspiration of the bead diluent from 100 μL conjugated beads (2500 beads/μl) followed by addition of 20 μL biotinylated antibody (0.1 μg/ml) and 100 μl 4-fold diluted sample (or undiluted calibrator) to the bead pellet. For both samples and calibrator the same diluent was used [PBS; 0.1% Tween-20; 2% BSA; 10 μg/ml TRU Block (Meridian Life Science, Inc., Memphis, TN, USA)]. After a 47 cadances incubation (1 cadance=45 s) the beads were washed followed by addition of 100 μL of the streptavidin-conjugated ß-galactosidase (150 pM, Cat #: 100439, Quanterix). This was followed by a 7 cadences incubation and a wash. Prior to reading, 25 μL resorufin β-D-galactopyranoside (Cat #: 100017, Quanterix) was added. The calibrator curve was constructed using the standard from the NFL ELISA (NF-light®, UmanDiagnostics) in triplicate. The lower limits of detection and quantification, as defined by the concentration derived from the signal of blank samples (sample diluent)+3 and 10 standard deviations, were 0.97 and 2.93 pg/mL, respectively. For a QC sample with a concentration of 13.0 pg/mL, repeatability was 14.0% and intermediate precision was 15.7%. For a QC sample with a concentration of 131.8 pg/mL, repeatability was 13.3% and intermediate precision was 13.3%. All measurements were performed by board-certified laboratory technicians who were blinded to clinical data in one round of experiments using one batch of reagents.

MRI Acquisition and Analysis

Serial MRI scans were obtained on 33 of the 48 participants, firstly at the time of the blood sample and then again approximately 1 year later (mean interval±SD=1.33±0.46 years). All scans were performed on the same 3T Siemens TIM Trio scanner using a 32-channel phased array headcoil. A sagittal 3D MP-RAGE T1-weighted volumetric MRI (echo time/repetition time/inversion time=2.9/2200/900 ms, dimensions of 256×256×208, voxel size of 1.1×1.1×1.1 mm) was acquired. Images were visually checked for artifact. Whole brain and ventricular volumes were calculated using a semi-automated method (Freeborough P A, Fox N C, Kitney R I Interactive algorithms for the segmentation and quantitation of 3-D MRI brain scans. Comput Methods Programs Biomed 1997; 53:15-25). All volumes were corrected for total intracranial volume (TIV). Annualized rates of whole brain and ventricular volume change during the inter-scan interval were calculated using the boundary shift interval (BSI)—a registration-based method of within subject volume change (Freeborough P A, Fox N C The boundary shift integral: an accurate and robust measure of cerebral volume changes from registered repeat MRI. IEEE Trans Med Imaging 1997; 16:623-629).

Statistical Analysis

The primary objective of the study was to compare serum NfL between symptomatic mutation carriers, pre-symptomatic mutation carriers, and healthy controls (i.e. gene negative family members). A generalized least squares linear regression model, which does not assume constant variance of residuals, was used to compare NfL between the groups, adjusting for age and gender (an extension of the t-test/ANOVA model that allows different variances in each group). Pairwise differences in means were used to examine the evidence for a difference in NfL between each pair of groups. No adjustment was made for multiple testing.

Spearman correlation coefficients were calculated to assess the relationship between EYO and NfL, first across all mutation carriers and then in pre-symptomatic carriers only. This approach was also used for NfL and cognitive measures, including estimated change in IQ (calculated by subtracting the predicted premorbid IQ measured by the NART from the actual IQ measured by WASI), recognition memory (an average of scores from RMT faces and RMT words), MMSE and CDR SOB. Finally, we assessed whether any correlation existed between NfL and the structural neuroimaging measures.

We calculated Spearman correlation coefficients for each imaging measure against EYO, including only pre-symptomatic participants. In order to allow the results to be comparable with serum NfL, we also repeated the analysis for serum NfL against EYO, but this time only included the pre-symptomatic individuals who had also had imaging.

Results

Participants' demographic details, cognitive test scores, neuroimaging measures, and serum NfL values are shown in the Table 1 at FIG. 4 and FIG. 1.

The mean EYO of the pre-symptomatic mutation carriers was 9.6 years. Adjusting for age and gender, serum NfL concentrations were significantly higher in symptomatic mutation carriers compared with both pre-symptomatic mutation carriers ($p<0.0001$) and non-carrier controls ($p<0.0001$). Pre-symptomatic mutation carriers had significantly higher NfL levels than controls (16.7 pg/mL vs. 12.7 pg/mL, $p=0.007$).

Across all mutation carriers, EYO correlated with serum NfL. (Spearman's $R=0.81$, $p<0.0001$), as illustrated in FIG. 2. FIG. 3 shows scatter plots of serum NfL against different cognitive and imaging measures. There was significant correlation between serum NfL and cognitive measures, including MMSE ($R=-0.62$, $p=0.0001$), CDR sum of boxes ($R=0.79$, $p<0.0001$), and estimated change in IQ ($R=-0.48$, $p=0.005$), with only a trend for the recognition memory score ($R=-0.34$, $p=0.056$). In mutation carriers, there was a significant correlation in mutation carriers between NfL and neuroimaging measures, including baseline whole brain volume ($R=-0.66$, $p=0.0005$), baseline ventricular volume ($R=0.57$, $p=0.005$), subsequent rate of change in whole brain volume ($R=0.54$, $p=0.0091$), and subsequent rate of change in ventricular volume ($R=0.58$, $p=0.005$).

When including pre-symptomatic participants only, there remained a significant correlation between NfL and EYO ($R=0.55$, $p=0.014$). There was also a significant correlation between NfL and baseline ventricular volume, but not with any of the other neuroimaging or cognitive measures.

When including only the 13 pre-symptomatic individuals who had also had serial imaging, there remained a significant correlation between serum NfL and EYO ($R=0.73$, $p=0.005$). However, when assessing the correlation between each of the four imaging measures and EYO in the same 13 pre-symptomatic individuals, none of them were statistically significant (table 2 at FIG. 5).

Longitudinal data derived from samples taken at two time points from 32 of the subjects described above show that serum NfL concentrations start to increase approximately 5 to 10 years prior to EYO in mutation carriers (FIG. 6).

Discussion

Using a recently developed, ultrasensitive immunoassay, we found that serum NFL concentrations are raised in FAD, and become elevated prior to the onset of symptoms. Elevated NfL levels were identified in both symptomatic and pre-symptomatic mutation carriers; the pre-symptomatic individuals being on average nine years from predicted symptom onset. Serum NfL correlated significantly with a surrogate measure of disease stage (EYO), CDR SOB, and with various cognitive measures. There was also a correlation between serum NfL and neuroimaging markers of AD-related neurodegeneration, both in terms of cross-sectional volumes and subsequent rates of atrophy. This suggests that serum NfL concentrations not only reflect the presence or absence of disease, but may also provide information pertaining to disease severity and/or intensity of loss.

The serum NfL concentrations we measured in symptomatic FAD would appear to be similar to those measured in previous studies of sporadic AD (Gaiottino J et al., supra; Bacioglu M. et al., supra). However, here we surprisingly show that the increase in serum NfL begins a number of years before the onset of symptomatic disease, and is associated with time to/from symptom onset. The progressive pre-symptomatic rise that we observed is consistent with proposed models of pre-symptomatic AD neurodegeneration (Jack C R, Jr., Knopman D S, Jagust W J, et al. Hypothetical model of dynamic biomarkers of the Alzheimer's pathological cascade. Lancet Neurol 2010; 9:119-128), with the NfL rise likely to reflect early axonal breakdown (Sjogren M, Blomberg M, Jonsson M, et al. Neurofilament protein in cerebrospinal fluid: a marker of white matter changes. J Neurosci Res 2001; 66:510-516).

The finding that serum NfL correlates with cognitive measures known to be sensitive to AD-related decline, supports the clinical relevance of NfL. Whilst early cognitive changes in FAD are relatively focal, most commonly involving episodic memory (Fox N C, Warrington E K, Seiffer A L, Agnew S K, Rossor M N. Pre-symptomatic cognitive deficits in individuals at risk of familial Alzheimer's disease. A longitudinal prospective study. Brain 1998; 121 (Pt 9):1631-1639), we found that serum NfL correlated more strongly with global cognitive measures than with memory scores. This may relate to NfL's role throughout the brain as an essential component of axonal stability, with initial rise possibly reflecting subtle widespread breakdown of neural networks (Warren J D, Rohrer J D, Schott J M, Fox N C, Hardy J, Rossor M N. Molecular nexopathies: a new paradigm of neurodegenerative disease. Trends Neurosci 2013; 36:561-569), rather than focal atrophy.

The possibility that elevated serum NfL levels reflect global, rather than focal, neurodegeneration is also supported by its correlation with whole brain and ventricular atrophy, which measures of global neurodegeneration.

Whilst serum NfL correlated with disease stage (i.e. EYO) even when only including the pre-symptomatic group, the imaging and cognitive measures did not. This indicates that, unlike the imaging and cognitive measures used, serum NfL was sensitive enough to show significant progressive change during this pre-symptomatic phase. Serum NfL may therefore be more sensitive to early neurodegeneration than currently widely used imaging and cognitive measures.

When measured in the CSF of individuals with mild cognitive impairment, NfL has been found to be predictive of subsequent progression to AD dementia (Zetterberg H et al., supra), with a recent meta-analysis showing it to have comparable discriminatory power to the well-established CSF AD biomarkers of $A\beta_{1-42}$, total tau and phosphotau (Olsson B et al., supra). Recent studies comparing serum NfL measurement in CSF and serum have shown that they correlate closely, which implies that serum NfL may similarly have the ability to predict subsequent progression.

A study in an FAD mouse model, which knocked out the NfL gene, found that NfL deficiency significantly increased AD-related neurodegeneration, thus highlighting NfL's central role in maintaining neuronal structure in AD (Fernandez-Martos C M, King A E, Atkinson R A, Woodhouse A, Vickers J C. Neurofilament light gene deletion exacerbates amyloid, dystrophic neurite, and synaptic pathology in the APP/PS1 transgenic model of Alzheimer's disease. Neurobiol Aging 2015; 36:2757-2767). In APP/PS1 mice, serum NfL levels in the blood have been shown to rise early in the disease, and to be closely associated with the progression of underlying AD pathology (Bacioglu M et al., supra). Furthermore, the same study showed serum NfL concentrations fell in response to anti-Aβ immunotherapy; the authors suggesting that serum NfL may be a marker of treatment response.

There are obvious benefits to identifying biomarkers that can be measured in blood (Consensus report of the Working Group on: "Molecular and Biochemical Markers of Alzheimer's Disease", supra). The search for sensitive blood-based AD biomarkers has therefore been a research area of great interest in recent times, with numerous candidates suggested (Lista S, O'Bryant S E, Blennow K, et al. Biomarkers in Sporadic and Familial Alzheimer's Disease. J Alzheimers Dis 2015; 47:291-317). However, recent comprehensive meta-analysis of blood-based markers showed only total tau to be able to reliably differentiate AD from healthy controls (Olsson B. et al., supra; Zetterberg H, Wilson D, Andreasson U, et al. Plasma tau levels in Alzheimer's disease. Alzheimers Res Ther 2013; 5:9); moreover blood tau has only proven useful at identifying AD in established dementia cases, and there is often overlap between patients and control groups (Olsson B. et al., supra; Lista S et al., supra). Studies attempting to measure levels of Aβ, the other core molecular marker of AD pathology, have so far produced conflicting results, with no strong overall evidence of a difference between AD and controls (Olsson B. et al., supra; Lista S et al., supra). Also, as cerebral Aβ deposition is thought to plateau some time before the onset of symptomatic disease, (Villemagne V L et al., supra; Bateman R J et al., supra), it may not be effective in tracking disease progression unless very early in disease. A marker of downstream neurodegeneration, such as NfL, which more closely reflects ongoing (and global) disease activity, may therefore be more useful as a clinical trial outcome measure.

In conclusion, here we show, for the first time, using a new ultrasensitive assay, that serum NfL concentration is increased in FAD even prior to symptomatic disease, and correlates with the number of years to/from predicted symptom onset. Serum NfL also correlated with neuroimaging and cognitive markers of disease severity. Our findings support the use of serum NfL as an easily accessible biomarker of early AD-related neurodegeneration.

Our study presents the first assessment of the utility of measuring serum NfL, using a new ultrasensitive assay, to detect early AD-related neurodegeneration. Our results show that serum NfL is elevated a number of years before the onset of clinical symptoms. We also show that serum NfL correlates very closely with number of years to/from estimated symptom onset, suggesting that it is able to track disease progression. Serum NfL is also found to correlate closely with current validated measures of AD severity, including structural imaging measures of atrophy and cognitive test scores. However, in the pre-symptomatic period, serum NfL may be more sensitive to neurodegenerative change than these more established measures.

Following our study it is now evident that serum NfL progressively rises over the 10 year period prior to the onset of symptomatic disease and correlates with other markers of neuronal loss. The current evidence therefore supports the use of serum NfL as an easily accessible biomarker of AD neurodegeneration throughout both pre-symptomatic and symptomatic disease.

The invention claimed is:

1. A method for detecting neurofilament-light (NfL) protein in a blood sample from a pre-symptomatic human individual known to have a family history of Alzheimer's disease or a genetic mutation known to predispose the human individual to develop Alzheimer's disease, wherein the pre-symptomatic human individual does not exhibit cognitive impairment, the method comprising:
   a) measuring NfL protein in the blood sample from the human individual using an immunoassay to detect an amount or concentration of NfL protein at below 1 pg/mL in the blood sample.

2. The method of claim 1, wherein the Alzheimer's disease is familial Alzheimer's disease.

3. The method of claim 1, further comprising
   b) repeating step a) one or more times.

4. The method of claim 1, wherein the blood sample is serum, plasma, or whole blood.

5. The method of claim 3, wherein the human individual is receiving prophylactic treatment for Alzheimer's disease.

6. An in vitro method for detecting neurofilament-light (NfL) protein in blood of a pre-symptomatic human individual known to have a family history of Alzheimer's disease or a genetic mutation known to predispose the human individual to develop Alzheimer's disease, wherein the pre-symptomatic human individual does not exhibit cognitive impairment, and wherein the method comprises performing an immunoassay to detect an amount or concentration of NfL protein at below 1 pg/mL, the method comprising:
   a) contacting (i) a blood sample obtained from the human individual, and (ii) a first antibody specific for NfL protein, whereby a complex comprising NfL protein and the first antibody is formed;
   b) optionally separating the complex comprising NfL protein and the first antibody for NfL protein from the remaining sample;
   c) contacting the complex comprising NfL protein and the first antibody for NfL protein with a second antibody specific for NfL protein, whereby a complex comprising NfL protein, the second antibody for NfL protein, and the first antibody for NfL protein is formed; and
   d) measuring the amount or concentration of the complex comprising NfL protein, the first antibody, and the second antibody.

7. The method of claim 6, wherein the blood sample is serum, plasma, or whole blood.

8. A method for detecting neurofilament-light (NfL) protein in a human individual comprising:
   a) obtaining a blood sample from the human individual; and
   b) measuring NfL protein in said sample using an immunoassay to detect an amount or concentration of NfL protein at below 1 pg/mL in the blood sample;
   wherein the human individual:
      i) does not exhibit cognitive impairment;
      ii) is pre-symptomatic for Alzheimer's disease; and
      iii) is known to have a family history of Alzheimer's disease or a genetic mutation known to predispose the human individual to develop Alzheimer's disease.

9. The method of claim 8, wherein:
   i) the human individual is at risk of developing one or more symptoms of Alzheimer's disease in one, two, three, four, or five years after said measuring;
   ii) the Alzheimer's disease is familial Alzheimer's disease; or
   iii) the blood sample is serum, plasma, or whole blood.

10. A method for prophylactic therapy of a pre-symptomatic human individual at risk of developing Alzheimer's disease, wherein the pre-symptomatic human individual does not exhibit cognitive impairment, the method comprising the steps:
   i) measuring an amount or concentration of neurofilament-light (NfL) protein in a blood sample obtained from the human individual;
   ii) detecting the human individual as being at risk of developing Alzheimer's disease by comparing the amount or concentration of the NfL protein determined in step i) to the amount or concentration of NfL protein in a control, wherein an increased amount or concentration of the NfL protein relative to the control is indicative of the future development of Alzheimer's disease; and
   iii) administering a prophylactic therapy for the Alzheimer's disease to the human individual who is detected as being at risk of developing Alzheimer's disease pursuant to step ii).

11. A method of prophylactic treatment for Alzheimer's disease of an individual determined to have an amount or concentration of neurofilament-light (NfL) protein in a blood sample from the individual that is greater than a control amount or concentration of NfL protein, the method comprising administering the prophylactic treatment to the individual.

12. A method for detecting neurofilament-light (NfL) protein in blood of a pre-symptomatic human individual known to have a family history of Alzheimer's disease or a genetic mutation known to predispose the human individual to develop Alzheimer's disease, wherein the pre-symptomatic human individual does not exhibit cognitive impairment, comprising the steps of:
   a) receiving a blood sample from the human individual at a first time point;
   b) measuring NfL protein in said sample using an immunoassay to detect an amount or concentration of NfL protein at below 1 pg/mL in the blood sample; and
   c) repeating method steps a) and b) one or more times.

13. The method of claim 12, wherein the individual is receiving prophylactic treatment for Alzheimer's disease.

14. A method comprising administering a prophylactic treatment for Alzheimer's disease to an individual determined to have an amount or concentration of neurofilament-light (NfL) protein in a blood sample from the individual that is greater than a control amount or concentration of NfL protein, wherein the prophylactic therapy comprises administration of aducanumab.

* * * * *